(12) United States Patent
Horiuchi et al.

(10) Patent No.: US 6,985,767 B2
(45) Date of Patent: Jan. 10, 2006

(54) LIVING BODY INFORMATION MEASURING APPARATUS, LIVING BODY INFORMATION MEASURING METHOD, BODY FAT MEASURING APPARATUS, BODY FAT MEASURING METHOD, AND PROGRAM RECORDING MEDIUM

(75) Inventors: Motomi Horiuchi, Sakurai (JP); Shinji Uchida, Neyagawa (JP)

(73) Assignee: Matsushita Electric Industrial Co., Ltd., Osaka (JP)

( * ) Notice: Subject to any disclaimer, the term of this patent is extended or adjusted under 35 U.S.C. 154(b) by 282 days.

(21) Appl. No.: 10/412,680

(22) Filed: Apr. 14, 2003

(65) Prior Publication Data

US 2004/0039287 A1 Feb. 26, 2004

Related U.S. Application Data

(63) Continuation of application No. 09/469,219, filed on Dec. 22, 1999, now Pat. No. 6,584,340.

(30) Foreign Application Priority Data

Dec. 24, 1998 (JP) .............................. H10-367565

(51) Int. Cl.
*A61B 6/00* (2006.01)
(52) U.S. Cl. ...................... 600/476; 600/407; 600/408; 600/473; 600/475; 600/310; 606/1; 607/88; 607/89; 607/94; 356/39; 356/40; 356/41; 250/340; 250/358.1
(58) Field of Classification Search ................ 600/310, 600/407–482; 606/1; 607/88, 89, 94; 356/39–41; 250/340, 358.1
See application file for complete search history.

(56) References Cited

U.S. PATENT DOCUMENTS

| | | | |
|---|---|---|---|
| 4,850,365 A | 7/1989 | Rosenthal | |
| 4,928,014 A | 5/1990 | Rosenthal | |
| 4,990,772 A | 2/1991 | Rosenthal | |
| 5,014,713 A | 5/1991 | Roper et al. | |
| 5,299,570 A | 4/1994 | Hatschek | |
| 5,365,066 A | 11/1994 | Krueger, Jr. et al. | |
| 5,490,506 A | 2/1996 | Takatani et al. | |
| 5,676,143 A | 10/1997 | Simonsen et al. | |
| 6,584,340 B1 * | 6/2003 | Horiuchi et al. ............ 600/473 |

FOREIGN PATENT DOCUMENTS

EP 0 516 251 3/1992

(Continued)

OTHER PUBLICATIONS

Article entitled "Photon migration in the presence of a single defect: a perturbation analysis" by Feng et al.; from Applied Optics; vol. 34, No. 19, Jul. 1, 1995.

*Primary Examiner*—Ali Imam
*Assistant Examiner*—William C Jung
(74) *Attorney, Agent, or Firm*—Smith, Gambrell & Russell, LLP

(57) ABSTRACT

A body fat measuring apparatus is provided with a light emitting device 1 for projecting light rays to a subject's tissue, light receiving devices 3 and 4 for detecting a transmitted light ray having passed through the subject's tissue and/or a reflected light ray reflected inside the subject's body, and a CPU 6 for calculating the subject's subcutaneous fat thickness and/or body fat percentage by performing an operation by use of the detection results of the light receiving devices 3 and 4. The light receiving devices 3 and 4 are situated at different distances from the light emitting device 1.

15 Claims, 47 Drawing Sheets

FOREIGN PATENT DOCUMENTS

| | | |
|---|---|---|
| EP | 0 942 260 | 9/1999 |
| JP | 2648377 | 5/1997 |
| JP | 3035791 | 2/2000 |
| JP | 2000-155091 | 6/2000 |
| WO | WO 89 08428 | 9/1989 |
| WO | WO 98 44841 | 10/1998 |

\* cited by examiner

Fig. 5

SD9mm
Correction data processing not performed

| | Correction coefficient (R) | |
|---|---|---|
| | | 950nm |
| Subcutaneous fat thickness | | 0.6429 |
| Body fat percentage | | 0.7538 |

SD7mm
Correction data processing not performed

| | Correction coefficient (R) | |
|---|---|---|
| | | 950nm |
| Subcutaneous fat thickness | | 0.5624 |
| Body fat percentage | | 0.7276 |

SD5mm
Correction data processing not performed

| | Correction coefficient (R) | |
|---|---|---|
| | | 950nm |
| Subcutaneous fat thickness | | 0.4049 |
| Body fat percentage | | 0.6013 |

SD3mm
Correction data processing not performed

| | Correction coefficient (R) | |
|---|---|---|
| | | 950nm |
| Subcutaneous fat thickness | | 0.2674 |
| Body fat percentage | | 0.4424 |

Fig. 14

SD9mm/SD3mm
Correction data processing performed

| Correction coefficient (R) | |
|---|---|
| | 950nm |
| | 0.67 |
| Subcutaneous fat thickness | |

SD9mm/SD5mm
Correction data processing performed

| Correction coefficient (R) | |
|---|---|
| | 950nm |
| | 0.65 |
| Subcutaneous fat thickness | |

SD9mm/SD7mm
Correction data processing performed

| Correction coefficient (R) | |
|---|---|
| | 950nm |
| | 0.61 |
| Subcutaneous fat thickness | |

SD7mm/SD3mm
Correction data processing performed

| Correction coefficient (R) | |
|---|---|
| | 950nm |
| | 0.59 |
| Subcutaneous fat thickness | |

SD7mm/SD5mm
Correction data processing performed

| Correction coefficient (R) | |
|---|---|
| | 950nm |
| | 0.56 |
| Subcutaneous fat thickness | |

SD5mm/SD3mm
Correction data processing performed

| Correction coefficient (R) | |
|---|---|
| | 950nm |
| | 0.51 |
| Subcutaneous fat thickness | |

Fig. 21

| SD9mm Correction data processing not performed | | | SD7mm Correction data processing not performed | | | SD5mm Correction data processing not performed | | | SD3mm Correction data processing not performed | | |
|---|---|---|---|---|---|---|---|---|---|---|---|
| | Correction coefficient (R) | | | Correction coefficient (R) | | | Correction coefficient (R) | | | Correction coefficient (R) | |
| | | 650nm | | | 650nm | | | 650nm | | | 650nm |
| Subcutaneous fat thickness | | 0.5677 | Subcutaneous fat thickness | | 0.4963 | Subcutaneous fat thickness | | 0.3551 | Subcutaneous fat thickness | | 0.2298 |
| Body fat percentage | | 0.7308 | Body fat percentage | | 0.6885 | Body fat percentage | | 0.5594 | Body fat percentage | | 0.3978 |

Fig. 30

SD9mm/SD3mm
Correction data processing performed

| Correction coefficient (R) | 650nm |
|---|---|
| Subcutaneous fat thickness | 0.7019 |
| Body fat percentage | 0.8426 |

SD9mm/SD5mm
Correction data processing performed

| Correction coefficient (R) | 650nm |
|---|---|
| Subcutaneous fat thickness | 0.6912 |
| Body fat percentage | 0.7796 |

SD9mm/SD7mm
Correction data processing performed

| Correction coefficient (R) | 650nm |
|---|---|
| Subcutaneous fat thickness | 0.6712 |
| Body fat percentage | 0.7378 |

SD7mm/SD3mm
Correction data processing performed

| Correction coefficient (R) | 650nm |
|---|---|
| Subcutaneous fat thickness | 0.6575 |
| Body fat percentage | 0.8478 |

SD7mm/SD5mm
Correction data processing performed

| Correction coefficient (R) | 650nm |
|---|---|
| Subcutaneous fat thickness | 0.6293 |
| Body fat percentage | 0.7478 |

SD5mm/SD3mm
Correction data processing performed

| Correction coefficient (R) | 650nm |
|---|---|
| Subcutaneous fat thickness | 0.5647 |
| Body fat percentage | 0.8260 | ian# LIVING BODY INFORMATION MEASURING APPARATUS, LIVING BODY INFORMATION MEASURING METHOD, BODY FAT MEASURING APPARATUS, BODY FAT MEASURING METHOD, AND PROGRAM RECORDING MEDIUM This application is a continuation of a U.S. patent application Ser. No. 09/469,219 filed Dec. 22, 1999, which is now U.S. Pat. Ser. No. 6,584,340.

BACKGROUND OF THE INVENTION

1. Field of the Invention

The present invention relates to a living body information measuring apparatus and the like for noninvasively measuring a subject's living body information such as the pulse rate, the blood-sugar level, subject's subcutaneous fat thickness and fat percentage.

2. Related Art of the Invention

An apparatus for noninvasively measuring a subject's body fat percentage has previously been proposed.

For example, U.S. Pat. No. 4,990,772 proposes a method of measuring a subject's body fat percentage by use of near infrared rays. According to this United States Patent, near infrared rays used for ingredient analysis of food and the like are projected to a subject, and a specific wavelength component of the light having intruded into the subject is analyzed.

FIG. 45 shows the structure of a body fat percentage measuring apparatus according to the prior art. As shown in the figure, a pair of light emitting devices 12A and a light receiving device 13A are disposed on one end surface of a body 11A. In a cap 14A for protecting the end surface, an optical standard plate 15A is disposed so as to be opposed to the light emitting devices 12A and the light receiving device 13A. The light emitting devices 12A project near infrared rays to a subject being in intimate contact with the end surface of the body 11A. The projected light is reflected after intruding into the subject. The light receiving device 13A detects the reflected light. A microcomputer (not shown) incorporated in the body 11A calculates the subject's body fat percentage based on data on the subject's height and weight and the information on the reflected light detected by the light receiving device 13A. In the actual measurement, first, light projection and reflected light detection are performed with the cap 14A being fitted on the body 11A, and a reference value for the subsequent measurement is obtained. Thereafter, light projection to the subject and reflected light detection are performed.

However, in the above-described body fat measuring apparatus, light-shading is insufficient according to the subject's measured part such as an arm which is thin. Light-shading is also insufficient according to the angle at which the body fat measuring apparatus is pressed against the subject. Consequently, accurate data cannot be obtained.

Moreover, since it is necessary to perform measurement twice for adjustment and for actual measurement, a long time is required for the measurement.

Moreover, since the color of the skin differs among individuals, when the color of the skin is different among subjects, the body fat percentage detected by a body fat measuring apparatus that projects light from above the skin is naturally inaccurate.

Moreover, in the conventional body fat measuring apparatus, since near infrared rays (wavelength 950 nm) are used, when the measurement is performed at a very bright place, the light having propagated through the living body becomes a disturbance because of the property of near infrared rays of more excellently passing through living bodies than visible light, so that accurate measurement cannot be performed.

Moreover, since the conventional body fat measuring apparatus uses near infrared rays which is largely absorbed by fat component, when the subject persons have different fat quality, the amount of light becomes largely changed, and Then it is difficult to detect accurately the thickness of fat.

Moreover, since the intensity of the light source and the sensitivity of the light receiving portion vary with time, it is necessary to obtain the reference value for the subsequent measurement every measurement by projecting light with the cap being fitted on the body and detecting the reflected light from the standard plate, which is very cumbersome.

Moreover, when the optical standard plate becomes dirty for some reason, the measurement value significantly differs.

SUMMARY OF THE INVENTION

Accordingly, an object of the present invention is to provide a living body information measuring apparatus and the like capable of easily obtaining living body information with high accuracy.

The present invention (corresponding to claim 1) is a living body information measuring method wherein a plurality of paths from a light emitting portion to a light receiving portion are created, and based on a light reception signal, from a path with higher accuracy, of a plurality of light reception signals obtained from the paths, living body information is calculated by a signal processor.

Moreover, the present invention (corresponding to claim 6) is a living body information measuring apparatus comprising: a light emitting portion for projecting light rays to a subject; a light receiving portion for detecting, of the light rays, a transmitted light ray having passed through the subject or a reflected light ray; and a signal processor for calculating the subject's living body information by analyzing a light ray detected by the light receiving portion, wherein at least one of the number of light emitting portions and the number of light receiving portions is not less than two, and wherein the signal processor analyzes, of a plurality of light rays detected by the light receiving portion, a light ray with higher accuracy to calculate the subject's living body information.

Moreover, the present invention (corresponding to claim 9) is a body fat measuring apparatus comprising: a light emitting portion for projecting light rays to a subject's tissue; a light receiving portion for detecting, of the light rays, a transmitted light ray having passed through the subject's tissue and/or a reflected light ray reflected inside the subject's body; and signal processing operation means for calculating the subject's subcutaneous fat thickness and/or body fat percentage by performing an operation by use of a detection result of the light receiving portion, wherein either the number of light emitting portions or the number of light receiving portions is not less than two, and wherein the not less than two light emitting portions or light receiving portions are situated at different distances from corresponding light receiving portion or light emitting means.

Moreover, the present invention (corresponding to claim 20) is a body fat measuring method using a body fat measuring apparatus of the present invention, said body fat measuring method comprising the steps of: projecting light rays to the subject by the light emitting portion; detecting a transmitted light ray (and/or a reflected light ray) having arrived by way of the subject's skin or skin and a layer in the vicinity thereof by the first light receiving portion; detecting a transmitted light ray (and/or a reflected light ray) having arrived by way of the subject's skin and subcutaneous fat layer by the second light receiving portion; and calculating the subject's subcutaneous fat thickness or body fat percentage by the signal processing operation means by correcting a detection result of the second light receiving portion by a detection result of the first light receiving portion and performing an operation by use of a result of the correction.

Moreover, the present invention (corresponding to claim 21) is a body fat measuring method using a body fat measuring apparatus of the present invention, said body fat measuring method comprising: a step in which a light ray projected by the first light emitting portion is detected by the light receiving portion as a first transmitted light ray (and/or a reflected light ray) having passed through the subject's skin or skin and a layer in the vicinity thereof; a step in which a light ray projected by the second light emitting portion is detected by the light receiving portion as a second transmitted light ray (and/or a reflected light ray) having passed through the subject's skin and subcutaneous fat layer; and a step in which the subject's subcutaneous fat thickness or body fat percentage is calculated by the signal processing operation means by correcting a detection result obtained by the second light emitting portion and the light receiving portion by a detection result obtained by the first light emitting portion and the light receiving portion and performing an operation by use of a result of the correction.

The body fat measuring apparatus of the present invention as described above is provided with a light emitting portion for projecting light rays to the subject, a light receiving portion for detecting, of the light rays, a transmitted light ray having passed through the subject or a reflected light ray, and a signal processor for calculating the subject's living body information by analyzing the light detected by the light receiving portion. Two or more light receiving portions or light emitting portions are provided, and the body fat is calculated by use of a measurement value from the light receiving portions. Further, it is desirable to use a light emitting diode with a central wavelength of not more than 650 nm as the light emitting portion.

Moreover, the present invention (corresponding to claim 22) is a living body information measuring apparatus comprising: a light emitting portion for projecting light rays to a subject's tissue; a light receiving portion for detecting, of the light rays, a transmitted light ray having passed through the subject's tissue and/or a reflected light ray reflected inside the subject's body; and signal processing operation means for calculating the subject's living body information by performing an operation by use of a detection result of the light receiving portion, wherein either the number of light emitting portions or the number of light receiving portions is not less than two, wherein the not less than two light emitting portions or light receiving portions are situated at different distances from corresponding light receiving portion or light emitting portions, wherein light sources of the plurality of light emitting portions are the same, or photoelectric conversion devices of the plurality of light receiving portions are the same, and wherein one of outputs of the plurality of light emitting portions or outputs of the plurality of light receiving portions is corrected by another one of the outputs.

BRIEF DESCRIPTION OF THE DRAWINGS

FIG. 5 is a view showing a table of living body data in cases of the conventional apparatus where the wavelength used is 950 nm.

FIG. 14 is a view showing a table of living body data in cases of the present invention where the wavelength used is 950 nm.

FIG. 21 is a view of a table showing living body data in cases, although not of the conventional apparatus, where processing is performed with one light receiving portion and the wavelength used is 650 nm.

FIG. 30 is a view of a table showing living body data in cases of the present invention where the wavelength used is 650 nm.

FIG. 43' is a view similar to FIG. 43 that shows an alternative structure for the apparatus of FIG. 43.

FIG. 44' is a view similar to FIG. 44 that shows an alternative structure for the apparatus of FIG. 44.

EXPLANATION OF REFERENCE NUMERALS

Figure 1:
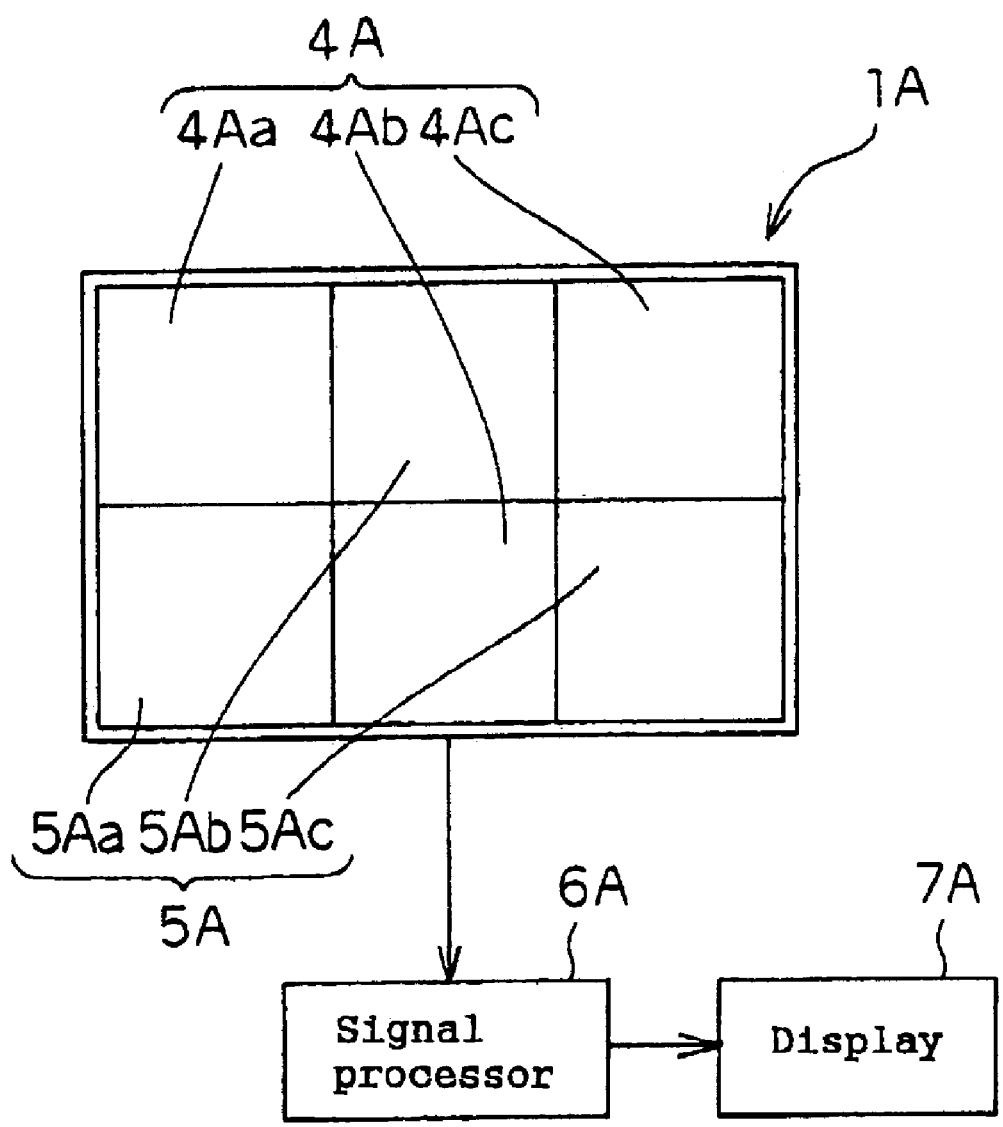
FIG. 1 is a schematic view showing the structure of a living body information measuring apparatus according to an embodiment of the present invention.

1A Sensor device
2A Subject
3A Blood vessel
4A, 4Aa, 4Ab, 4Ac, 4Ad, 4Ae, 4Af Light emitting portions
5A, 5Aa, 5Ab, 5Ac, 5Ad, 5Ae, 5Af Light receiving portions
6A Signal processor
7A Display
8A Light intensity operation unit
9A Living body information operation unit
10A Storage unit
11A Body
12A Light emitting device
13A Light receiving device
14A Cap
15A Optical standard plate
20A Blood vessel
21A Subject
1B Body
2B, 21B Light emitting devices
3B, 4B, 22B, 23B Light receiving devices
5B Amplifier
6B CPU
7B Display
1, 21 Bodies
2, 22 Light emitting portions
3, 28 Light receiving portions
4 Moving means
5 Attenuating filter
6, 29 Signal processors
7, 20 Displays
23, 24 Light directing means
25 Light quantity adjusting means
26 Hole
27 Moving means

PREFERRED EMBODIMENTS OF THE INVENTION

Preferred embodiments of the present invention will hereinafter be described in detail with reference to the drawings.

In FIG. 1, on an end surface of a sensor device 1A, a plurality of light emitting portions 4Aa to 4Ac and a plurality of light receiving portions 5Aa to 5Ac are alternately disposed so as to be in intimate contact with one another.

In actual measurement, the end surface is brought into intimate contact with the subject's skin. The light emitting portions 4Aa to 4Ac project light rays of a specific wavelength to the subject. The light ray projected by the light emitting portion 4Aa is incident on the light receiving portion 5Aa after passing through the subject. The light rays projected by the light emitting portions 4Ab and 4Ac are incident on the light receiving portions 5Ab and 5Ac, respectively, after passing through the subject. In that case, the light emission and the light reception are performed at staggered times. In a case where light rays are simultaneously projected from a plurality of light emitting portions, some contrivance is necessary such as varying the each wavelength among the light rays.

As described above, the light receiving portions 5Aa to 5Ac detect light rays projected by the light emitting portions 4Aa to 4Ac, respectively.

To ensure that the apparatus is in intimate contact with the subject, it is desirable that the light emitting portions and the light receiving portions be placed on the same plane.

To dispose a multiplicity of light emitting portions and light receiving portions on the end surface of the sensor device, it is desirable that the sizes thereof be minimized.

The light rays projected by the light emitting portions are selected based on what is measured by the apparatus. That is, when the body fat percentage is measured, small-size light emitting devices (LEDs) emitting light rays of wavelengths of 930 to 950 nm that are excellently absorbed by body fat are used as the light sources.

As the light receiving portions, for example silicon photodiode are used.

The light receiving portions 5Aa to 5Ac output signals responsive to the intensities of the detected light rays to a signal processor 6A.

The signal processor 6A performs excellent signal processing as described below.

For example, when a blood vessel is present in the subject's measured part, noise caused by the blood vessel can be avoided.

That is, the part of a blood vessel excellently absorbs, of the projected light, a component of a wavelength of 580 nm. On the other hand, the light absorption by body fat is at its peak when the wavelength is 930 to 950 nm. The light absorption by moisture is at its peak when the wavelength is 970 nm. Thus, the component of the light having passed through the part of a blood vessel and the component of the light having passed through other living body tissues are different in spectrum.

Therefore, when the ratio of intensity of a component, of a wavelength in the vicinity of 580 nm, of the light ray detected by a light receiving portion is lower than that of the light rays detected by the other light receiving portions or that of the projected light rays, the light ray detected by the light receiving portion is considered to have passed through a blood vessel. In the measurement of body fat, normally, such light must be excluded.

Therefore, according to the living body information measuring apparatus of the present invention, since a plurality of light rays having traveled along different paths are analyzed, of the light rays detected by the light receiving portions, the light ray considered to have passed through a blood vessel can be excluded so that the light rays detected by the other light receiving portions are analyzed. Consequently, body fat measurement can be performed with high accuracy.

Light rays having passed through foreign substances adhering to the surface of a living body, tumors, pimples, wounds and the like can be identified and excluded based on a similar principle.

Moreover, the living body information measuring apparatus of the present invention which is capable of detecting the subject's blood vessels as described above can be used not only for measuring the body fat but also for analyzing blood ingredients.

Specifically, by projecting by the light emitting portions light rays including wavelength components excellently absorbed by glucose, cholesterol, red blood corpuscles and the like together with the component of 580 nm excellently absorbed by the part of a blood vessel, the concentrations of these ingredients in the blood can be measured.

Specifically, to measure the blood-sugar level, that is, the concentration of glucose in the blood, a light ray of a component of a wavelength of 1600 nm is emitted to perform spectroscopic analysis. To measure the cholesterol level in the blood, a light ray of a wavelength of 960 nm is emitted to perform spectroscopic analysis.

In the cases of the blood vessel detection and the glucose concentration and cholesterol detection, contrary to the case of the body fat measurement, light not having passed through a blood vessel becomes noise for the light having passed through a blood vessel.

Figure 2:
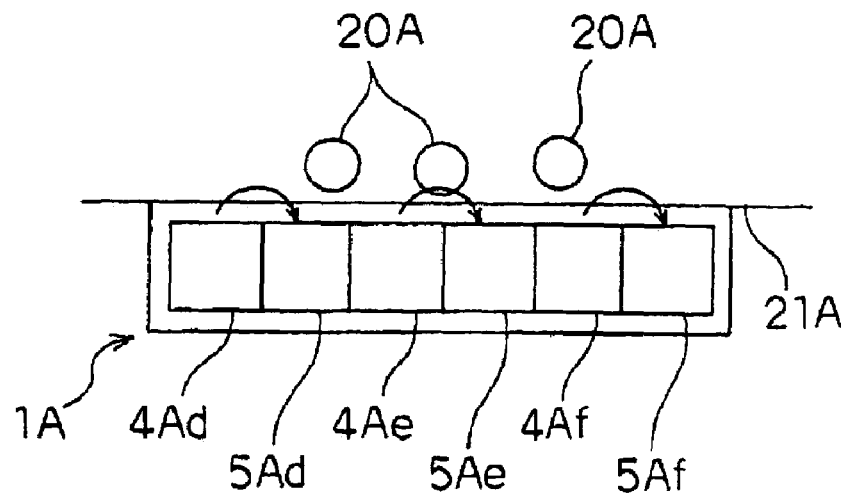
FIG. 2(a) is a cross-sectional view of an end of a sensor device used in the living body information measuring apparatus according to the embodiment of the present invention.
FIG. 2(b) is a block diagram showing the structure of a signal processor of the living body information measuring apparatus of FIG. 1.
Figure 2:
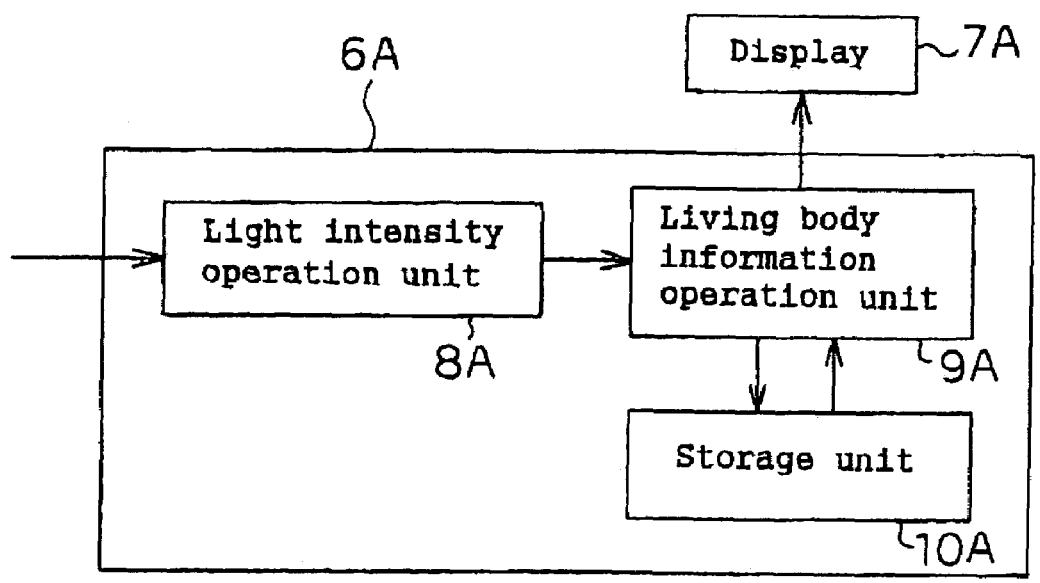

The signal processor 6A includes a light intensity operation unit 8A, a living body information operation unit 9A and a storage unit 10A as shown in FIG. 2.

The light intensity operation unit 8A monitors the input signal from the light receiving portion 5A and detects the start and the end of the measurement based on a fluctuation of the input signal. When an abnormal condition such as separation of the sensor device 1A from the subject is encountered during the measurement, the light intensity operation unit 8A detects that. On detecting the start of the measurement, the light intensity operation unit 8A outputs a signal responsive to the intensity of the light detected by the light receiving portion 5A to the living body information operation unit 9A.

The living body information operation unit 9A calculates living body information such as the body fat percentage based on the input signal. At this time, in the measurement of the body fat percentage, the living body information operation unit 9A identifies the light ray with higher accuracy by comparing a plurality of signals based on light rays having traveled along different paths with one another or comparing the signals with a preset reference value, and analyzes the light ray.

For example, the signal based on the light ray having passed through a vessel 20A of a subject 21A like the light ray projected from a light emitting portion 4Ae shown in FIG. 1(a) to be incident on a light receiving portion 5Ae is excluded, and living body information is calculated by using only the signals based on the light rays projected from light receiving portions 4Ad and 4Af to the subject 21A to be incident on light receiving portions 5Ad and 5Af, respectively.

On the contrary, in the measurement of blood ingredients, only the signal based on the light ray having passed through the blood vessel 20A is identified, and living body information such as the blood-sugar level is calculated based on the signal.

The obtained living body information is stored in the storage unit 10A having a magnetic recording medium, a semiconductor memory or the like.

The living body information obtained in the above-described manner is displayed on a display 7A such as a liquid crystal display so as to inform the subject, etc.

As described above, according to the present invention, a living body information measuring apparatus capable of easily obtaining living body information with high accuracy can be provided.

Another embodiment of the present invention will hereinafter be described with reference to the drawings.

Figure 3:
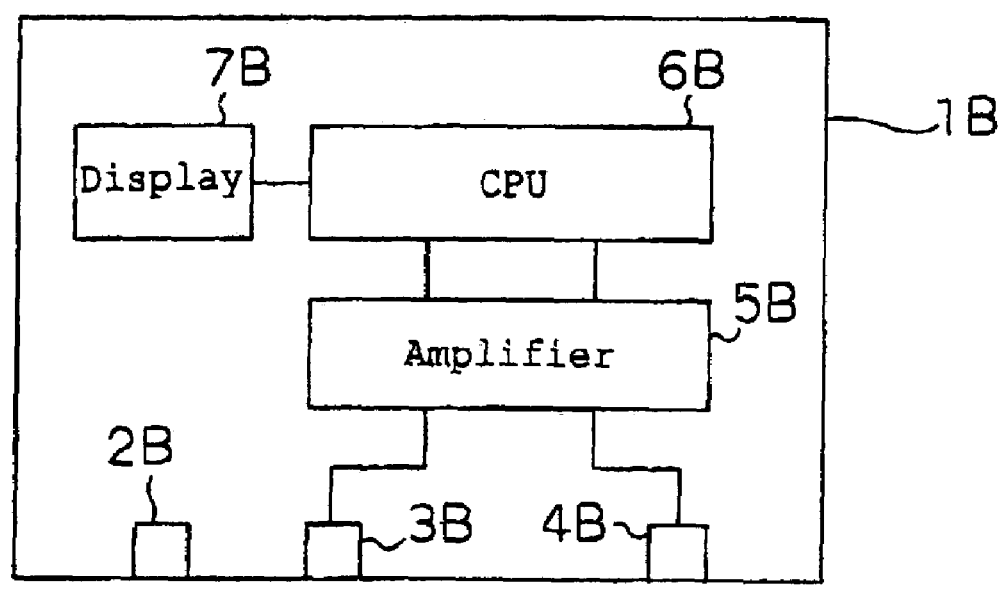
FIG. 3 is a view showing an outline of a body fat measuring apparatus according to an embodiment of the present invention.

A body fat measuring apparatus according to the embodiment of the present invention is shown in FIG. 3. A light emitting device 2B and light receiving devices 3B and 4B are disposed on one end surface of a body 1B. Moreover, an amplifier 5B, a central processing unit (CPU) 6B and a display 7B are disposed on the body 1B.

The basic operation of the body fat measuring apparatus of the embodiment having such a structure is as described below. The light emitting device 2B projects a visible light ray with a central wavelength of not more than 650 nm to the subject being in intimate contact with the end surface of the body 1B. As the light emitting device 2B, for example, a light emitting diode with a central wavelength of 635 nm (for example, FR1111C manufactured by Stanley) is used. As the light receiving devices 3B and 4B, for example, silicon photodiodes are used.

The light receiving device 3B is situated approximately 3 mm away from the light source. While the distance from the light source to the light receiving device 3B is not limited to 3 mm, it is desirable that the light receiving device 3B be situated within 5 mm from the light source.

The light receiving device 4B is situated approximately 9 mm away from the light source. While the distance from the light source to the light receiving device 4B is not limited to 9 mm like in the case of the light receiving device 3B, it is desirable that the light receiving device 4B be not less than 6 mm away from the light source.

The light projected from the light emitting device 23 intrudes into the subject, and then, part of the light is scattered and repetitively reflected to exit from the surface of the living body. The light receiving devices 3B and 4B detect the reflected light.

The light detected by the light receiving devices 3B and 4B is amplified by the amplifier 5A, and is corrected by the CPU 6B by dividing the output of the light receiving device 4B by the output of the light receiving device 3B, and is converted into the body fat amount or thickness, which is displayed on the display 7B.

Next, the operation principle of the body fat measuring apparatus and the body fat measuring method according to this embodiment will be mentioned. Generally, as described in "Photon Migration in the Presence of a Single Defect" by S. Feng et al., Applied Optics, Vol. 34, No. 19:3826–3837, it is known that when light emitted from a light source propagates through a living body to reach a light receiving device, letting the distance between the light source and the light receiving device be d, the light intrudes most deeply at a position which is apart by a half of the distance d from the light source. The light intrudes to a depth of approximately 0.35×d. In actuality, some light intrudes more deeply and some light propagates through a shallow part.

Therefore, when the distance between the light source and the light receiving portion is short, light having propagated through a part close to the surface of the living body is detected, and when the distance between the light source and the light receiving portion is long, light having propagated through a deep part of the living body is detected.

Figure 4:
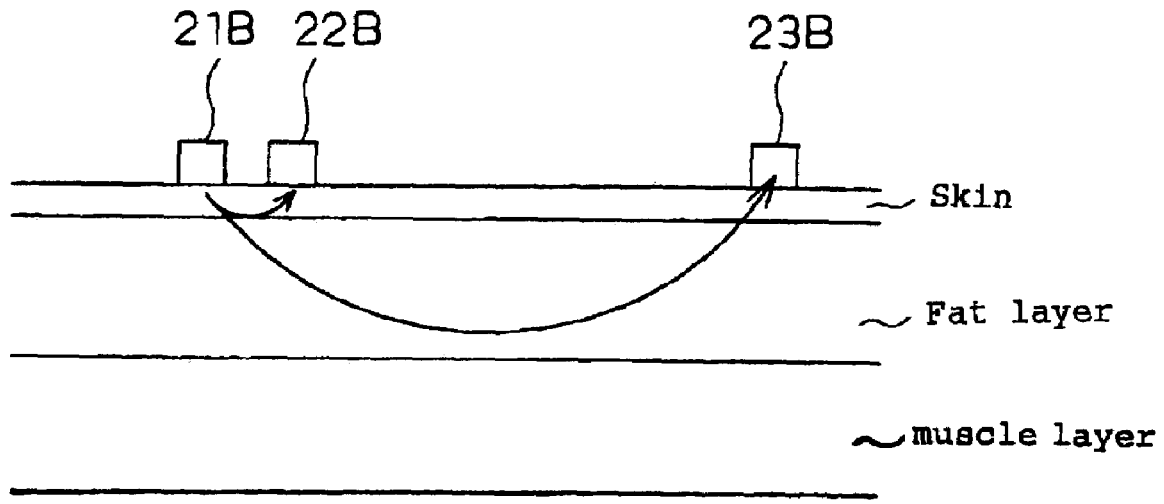
FIG. 4 is a view showing the principle of correction of individual differences among subjects in the body fat measuring apparatus according to an embodiment of the present invention.

The present invention applies such a characteristic of light propagation and the operation principle is described referring to FIG. 4 as a schematic figure.

Firstly the principle to be able to detect thickness is presumed by using light propagation route between the light emitting device 21B and the light receiving device 23B.

The light emitted from the device 23B enters into the surface of skin. The living body has light scattering property for near infrared ray or visible ray and then the entered light is scattered at the fat part. The light entering the fat part spreads and scatters and a part of the light reaches a muscle part. Since the muscle part has much blood and water and muscular fiber, the Reached light, is largely absorbed and scattered at the muscle part.

The light which does not reach the muscle part, that is, mainly penetrates the fat part is not so attenuated as that in the muscle part.

The distance between the light source and the first light receiving device closest to the light source is set to 3 mm and the light having propagated through a part close to the surface of the subject is detected, and the distance between the light source and the second light receiving device is set to 9 mm and the light having propagated mainly through a deep part of the living body is detected. Then, the detection value of the second light receiving device is divided by the detection value of the first light receiving device to correct the detection value of the second light receiving device, and the amount of body fat is calculated by use of the correction value, thereby improving the correlation with the true measurement value.

Next, the reason why this correction is effective will be inferred with reference to FIG. 4.

When between the emitting device 21B and the receiving device 22B which are near, the light from the device 21B enters into the skin and then is scattered to various directions and a part of these light enters into the receiving device 22B. Since the distance between the Device 21B and 22B strong light can be detected. Almost light which penetrates the skin and reaches the fat is scattered further and spreads. A few of the light can enters into the receiving device 22B but they are very weak in comparison with that of the light propagated near the skin and then almost lights scatter into deeper part and broad wise and do not reach the receiving device 22B.

That is it is presumed that between the emitting device 21B and the receiving device 22B the light propagates along or near the skin and then the light received at the receiving device 22B has many information about the skin and the part near the skin.

In the case of light propagation from the light emitting device 21B to a light receiving device 23B situated at a longer distance therefrom, it is roughly considered that after passing through the skin, light emitted from the light emitting device 21B reaches body fat in a deep part of the living body, continues traveling while being scattered and reflected at the body fat, and reaches the second light receiving device 23B after passing through the skin again.

That is it is presumed that the light reached the receiving device 23B is effected by the fat part which is positioned at a deep part of the living body as well as by the skin to the contrary to the light entering the receiving device 22B.

Both the lights which are entering into the receiving device 22B and the receiving device 23B have almost same skin informations or near skin informations.

Therefore it is presumed that the effect on account of the skin or the part near the skin can be cancelled by dividing the detected signal from the second device with the detected signal from the first device.

Therefore it is presumed that even when there is different skin color, different skin structure, pure effect from the fat part can be detected by the above correctness.

Test data of the present invention which confirms the effect of the body fat measuring apparatus and the body fat measuring method according to the embodiment will be explained.

The inventors measured the body fat percentages and the body fat thicknesses of fifteen subjects whose true body fat percentages and body fat thicknesses were previously known by use of the conventional measuring apparatus and the measuring apparatus of the present invention. Data on the relationship between the true values and the values calculated by the measuring apparatuses are graphed and tabulated as shown in FIGS. 5 to 42.

Further, for the data, the inventors obtained a correlation expression of an equation of first degree representing the true body fat percentages and body fat thicknesses, and the calculated values as accurately as possible by a mathematical method such as the method of least squares, and obtained the correlation coefficients of the equation of first degree.

FIGS. 5 to 13 show cases of the conventional apparatus where the wavelength used is 950 nm. FIGS. 14 to 20 show cases of the present invention where the wavelength used is 950 nm. FIGS. 21 to 29 show cases, although not of the conventional apparatus, where processing is performed with one light receiving device and the wavelength used is 650 nm. FIGS. 30 to 42 show cases of the present invention where the wavelength used is 650 nm. The body fat thickness and the body fat percentage were measured in all the cases except the cases of the present invention shown in FIGS. 14 to 20.

Figure 6:
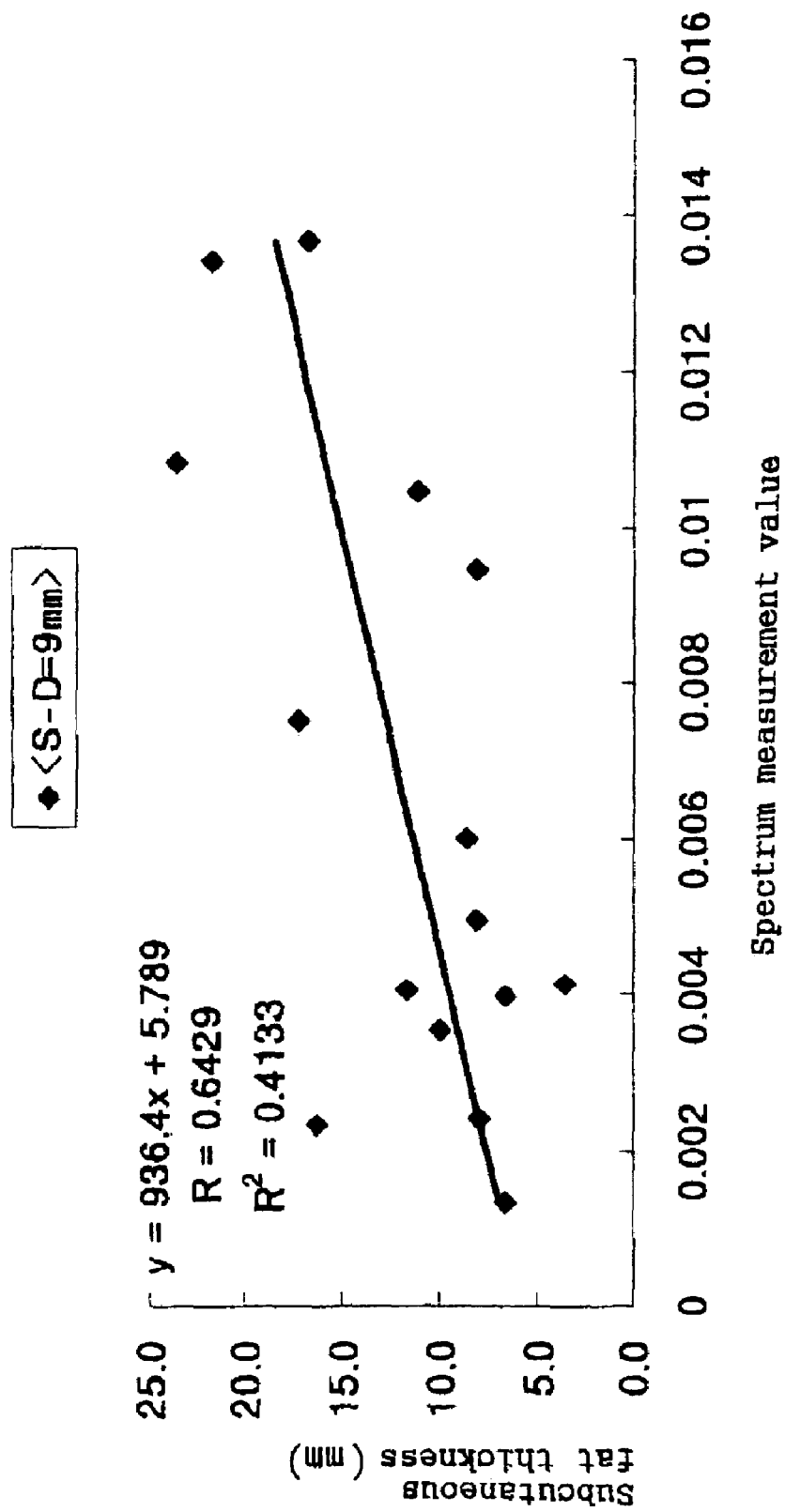
FIG. 6 is a graph of living body data in the case of the conventional apparatus where the wavelength used is 950 nm.
Figure 7:
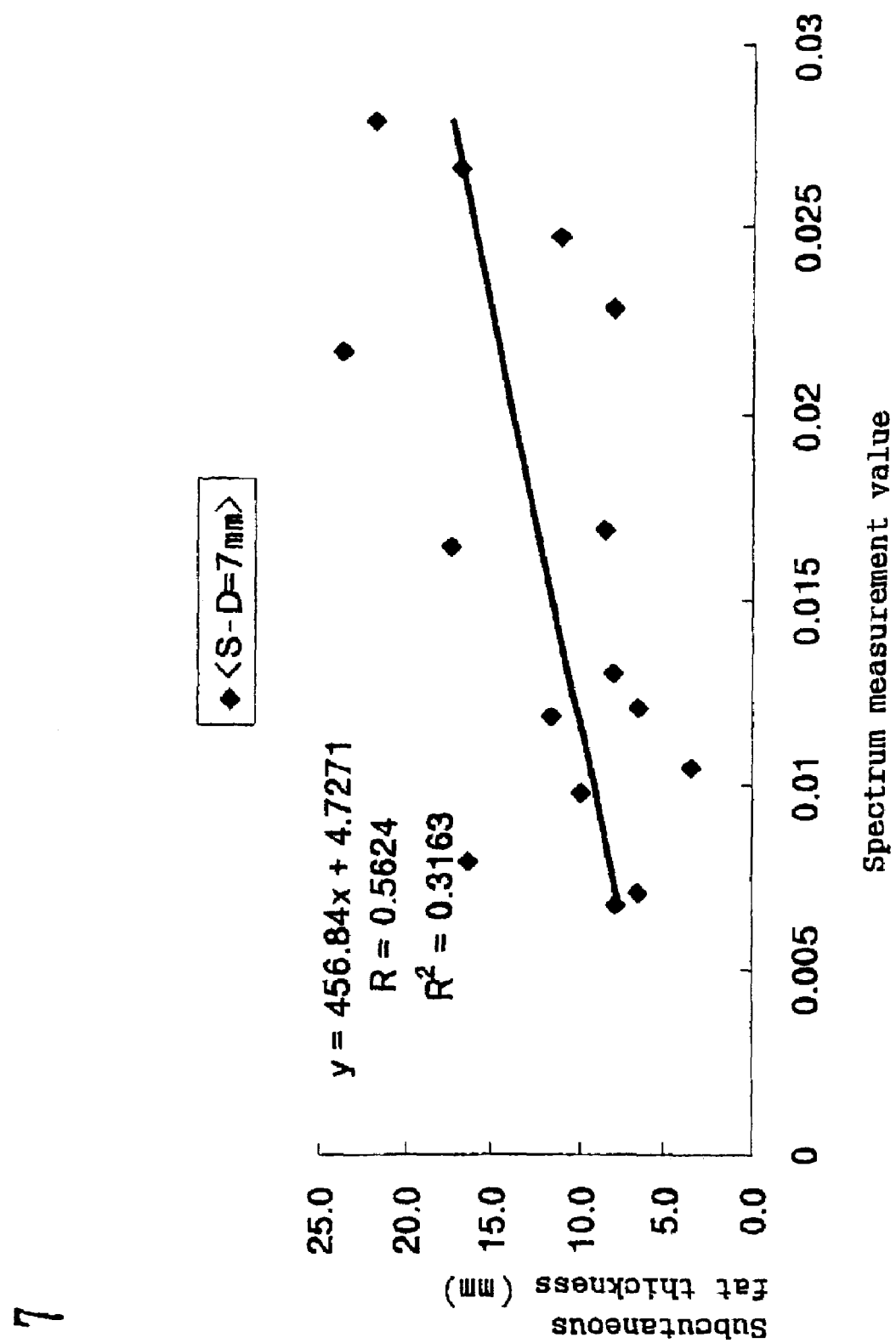
FIG. 7 is a graph of living body data in the case of the conventional apparatus where the wavelength used is 950 nm.
Figure 8:
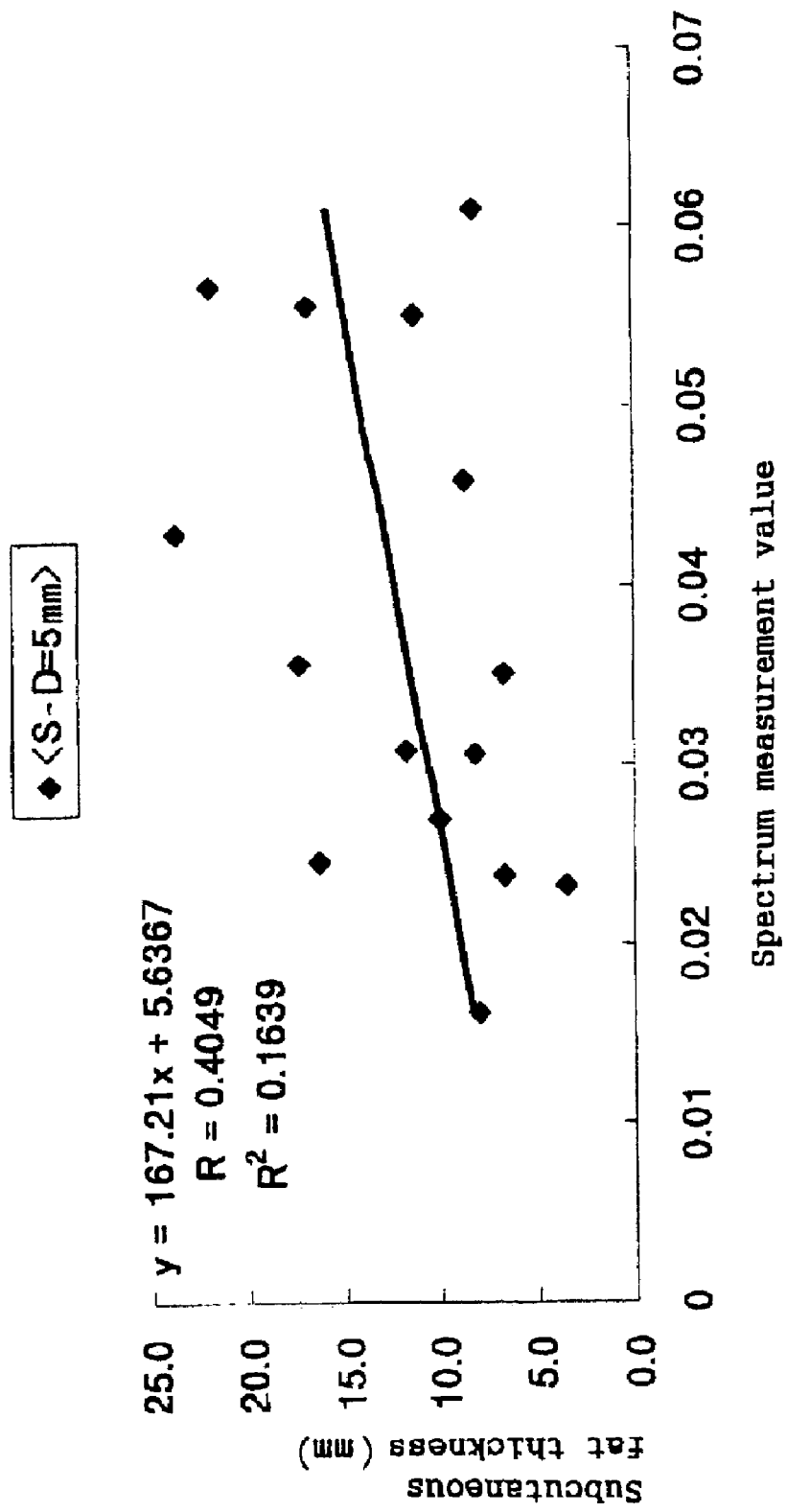
FIG. 8 is a graph of living body data in the case of the conventional apparatus where the wavelength used is 950 nm.
Figure 9:
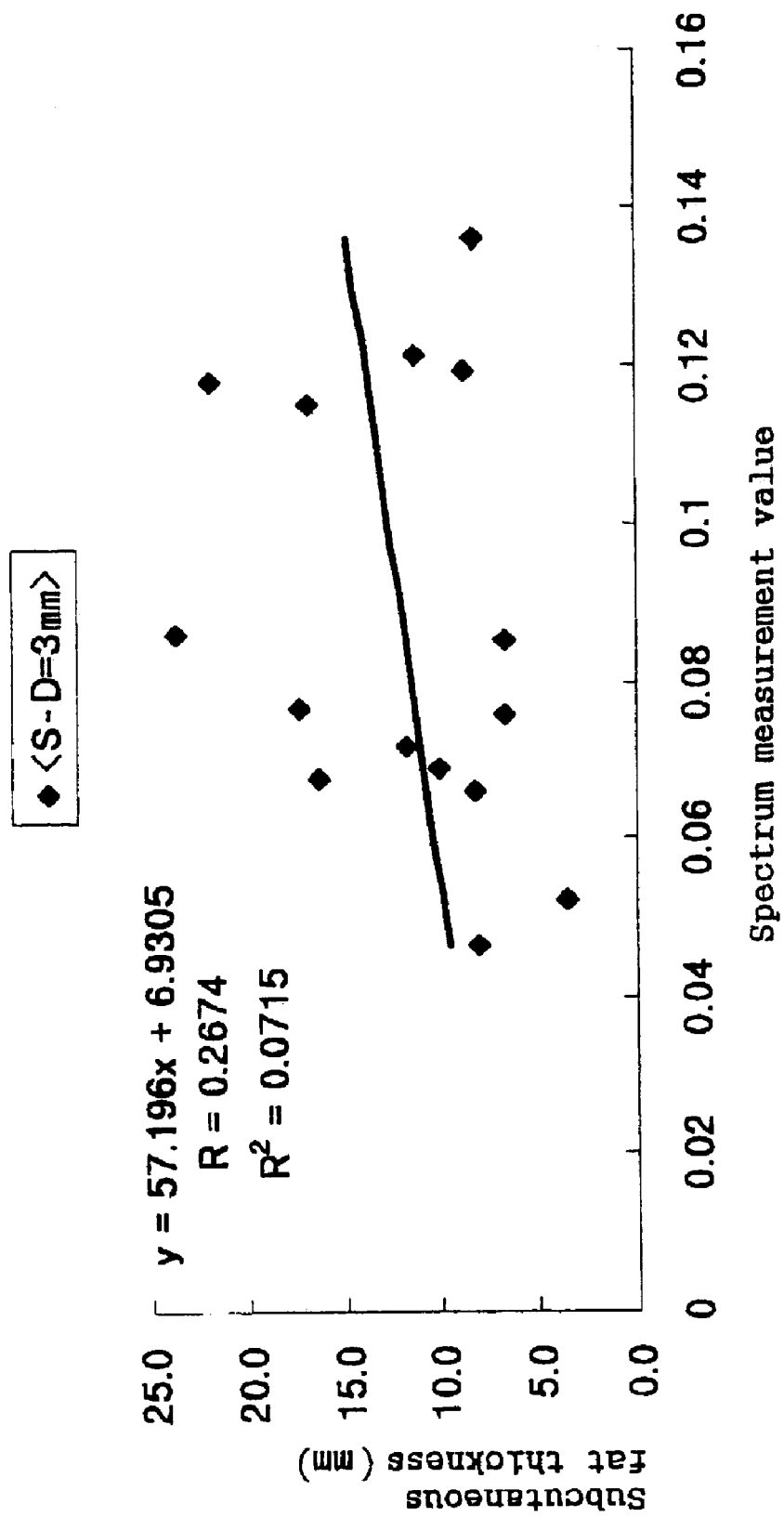
FIG. 9 is a graph of living body data in the case of the conventional apparatus where the wavelength used is 950 nm.
Figure 10:
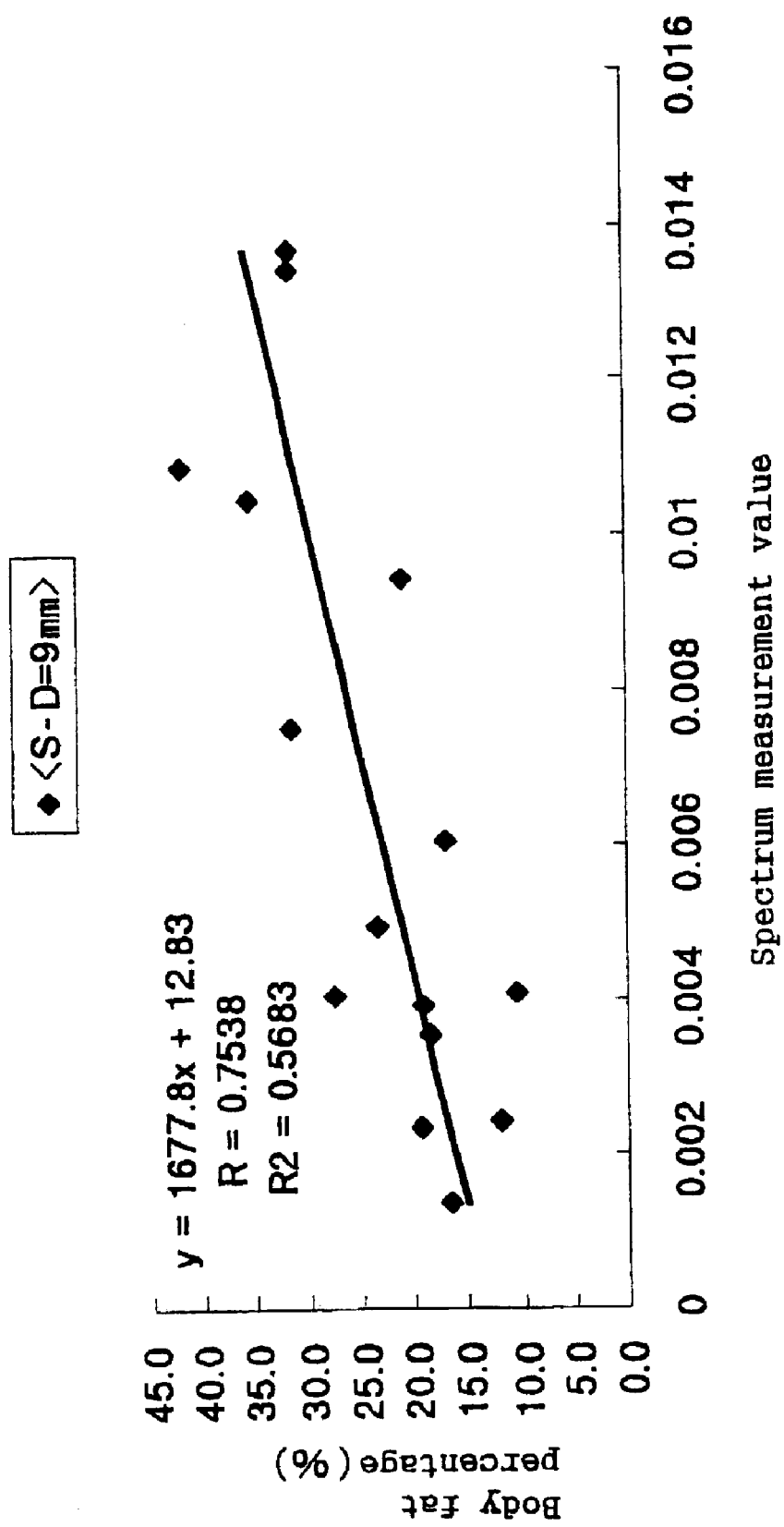
FIG. 10 is a graph of living body data in the case of the conventional apparatus where the wavelength used is 950 nm.
Figure 11:
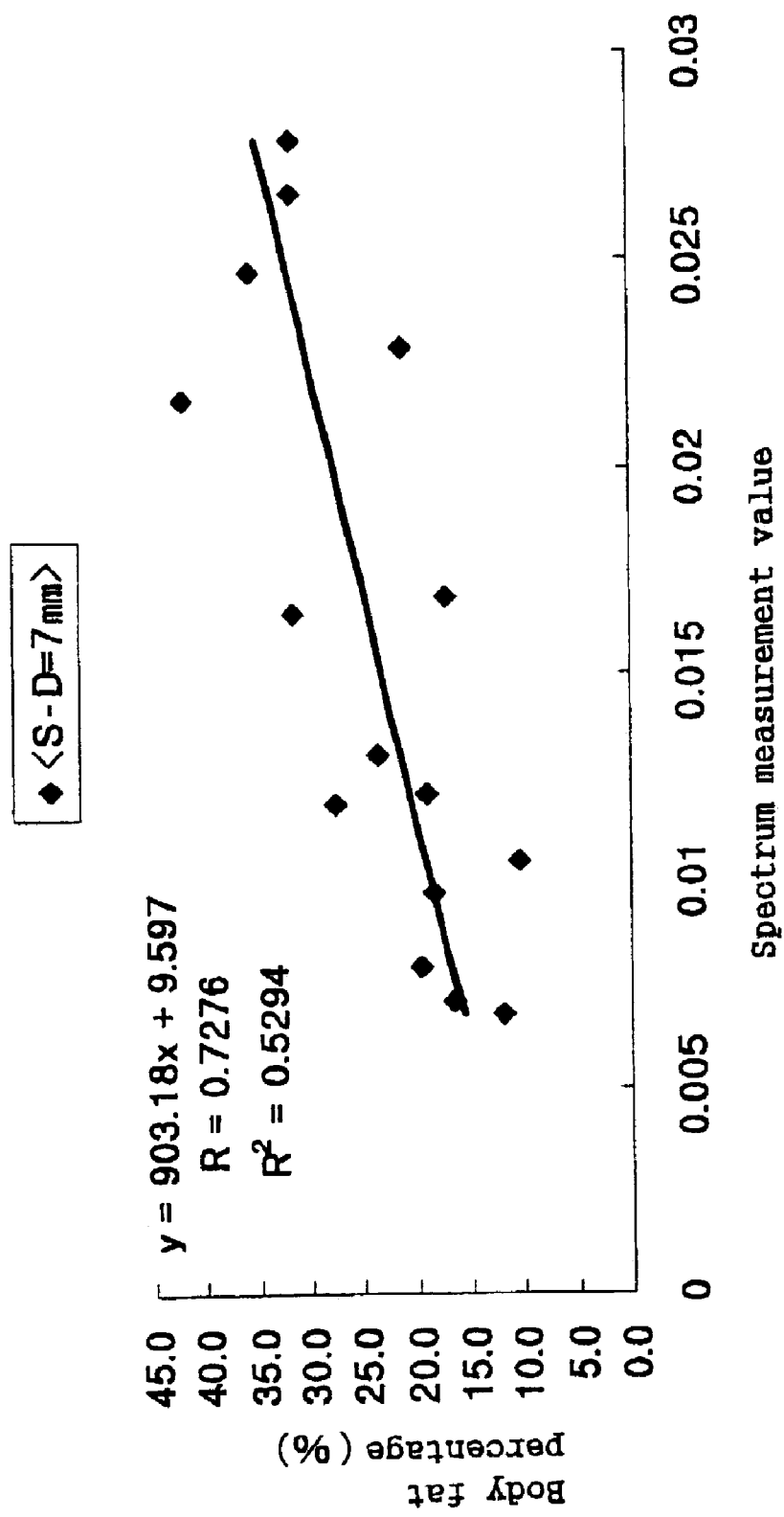
FIG. 11 is a graph of living body data in the case of the conventional apparatus where the wavelength used is 950 nm.
Figure 12:
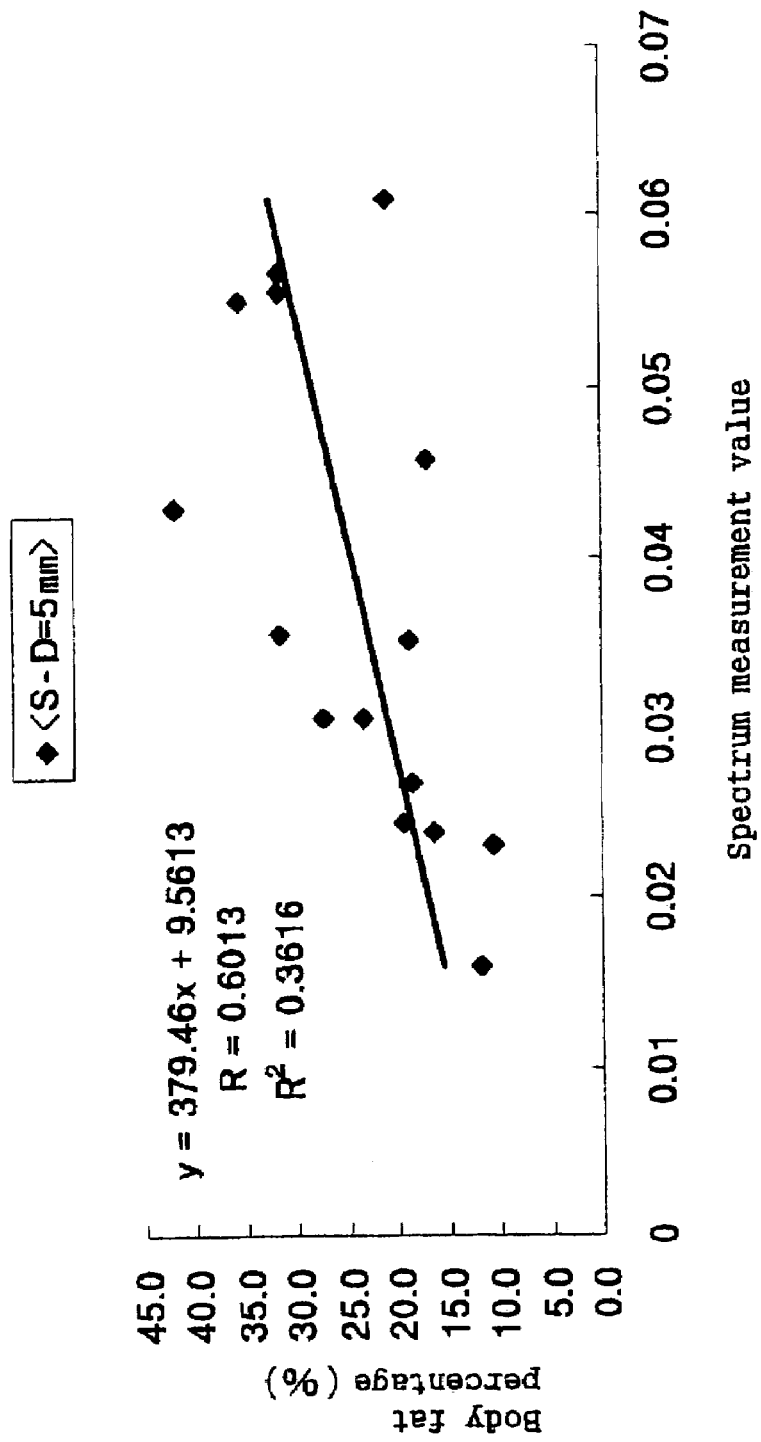
FIG. 12 is a graph of living body data in the case of the conventional apparatus where the wavelength used is 950 nm.
Figure 13:
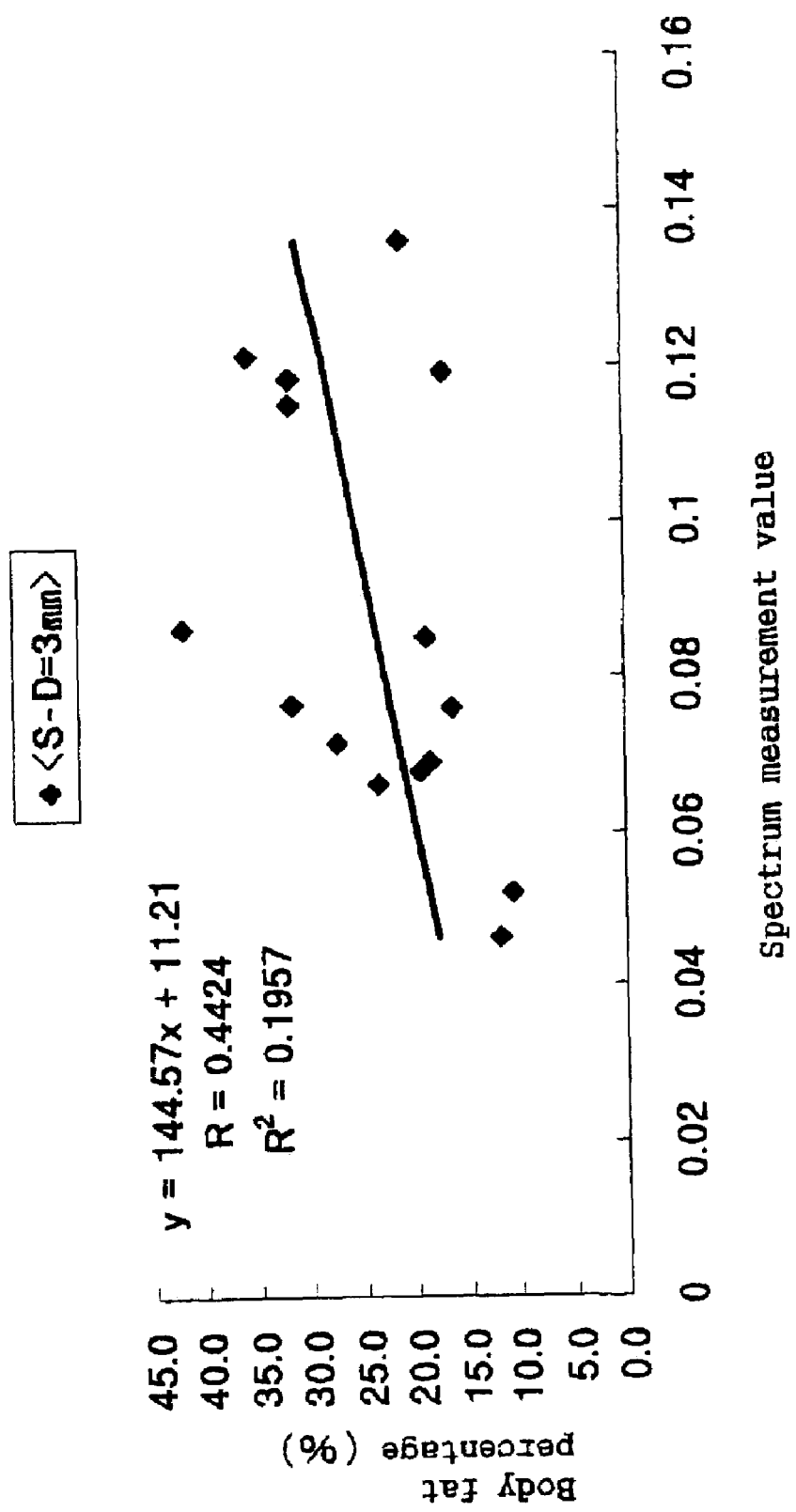
FIG. 13 is a graph of living body data in the case of the conventional apparatus where the wavelength used is 950 nm.

For example, the leftmost column in FIG. 5 showing the cases of the conventional apparatus where the wavelength is 950 nm shows a case where the number of light receiving portions is one and the light receiving portion is situated 9 mm away from the light emitting portion. The graphs corresponding to the case are shown in FIG. 6 (body fat thickness) and FIG. 10 (body fat percentage). For the body fat thickness, the correlation expression is $y=936.4x+5.789$, and the correlation coefficient R is $R=0.6429$. The other columns show cases where the distances are 7 mm, 5 mm and 3 mm, and the data are shown in a similar manner to the case of 9 mm.

Figure 15:
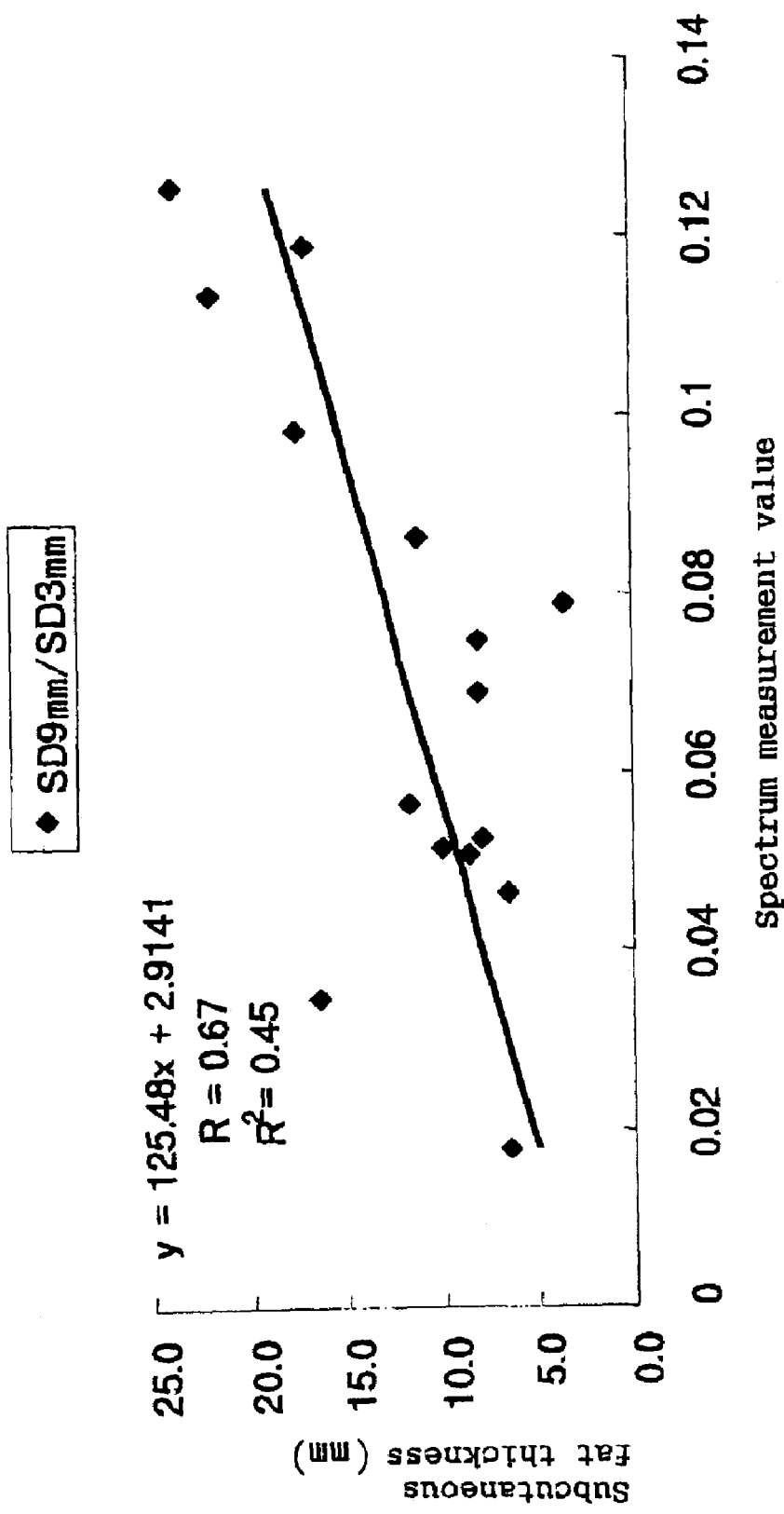
FIG. 15 is a graph showing living body data in the case of the present invention where the wavelength used is 950 nm.
Figure 16:
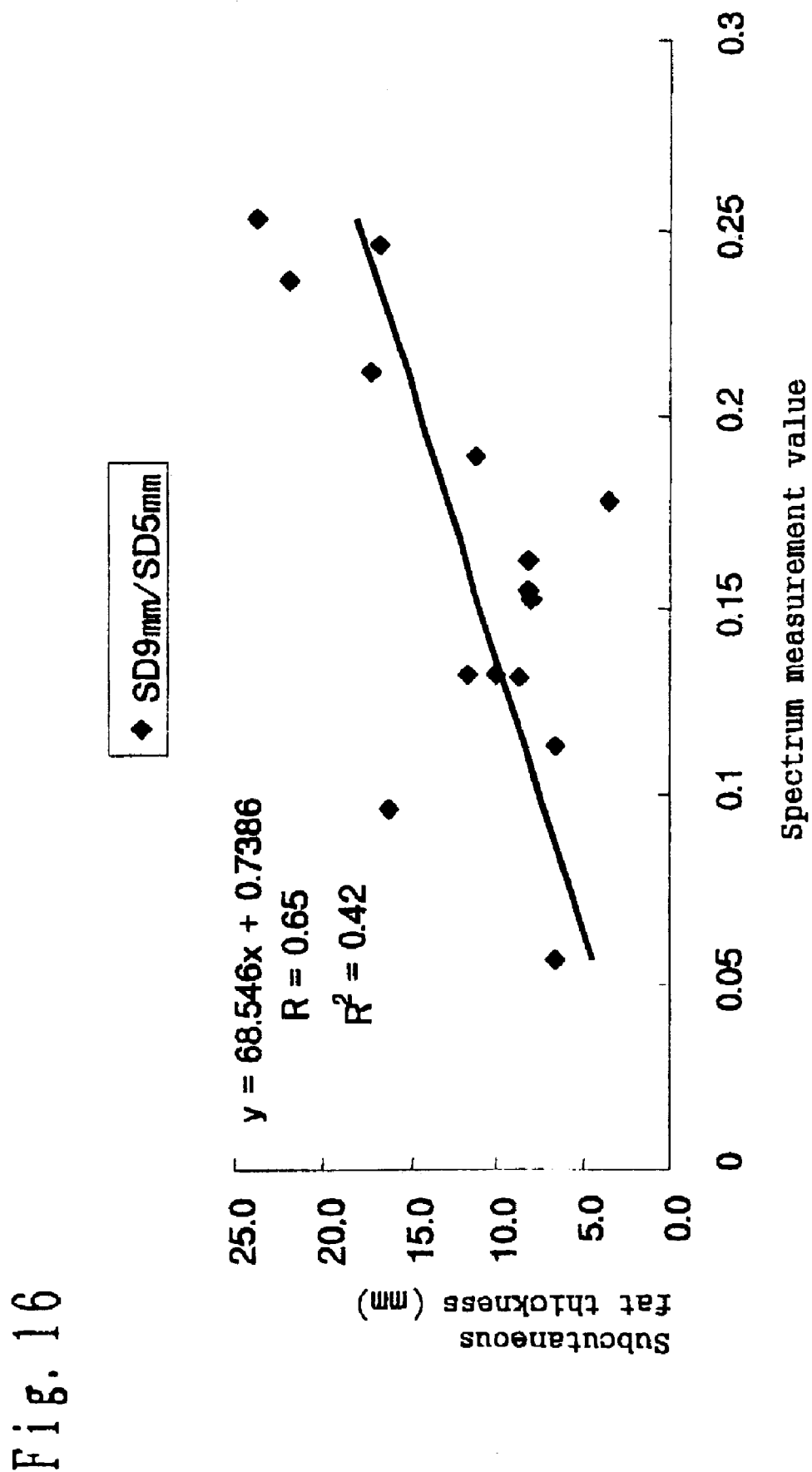
FIG. 16 is a graph showing living body data in the case of the present invention where the wavelength used is 950 nm.
Figure 17:
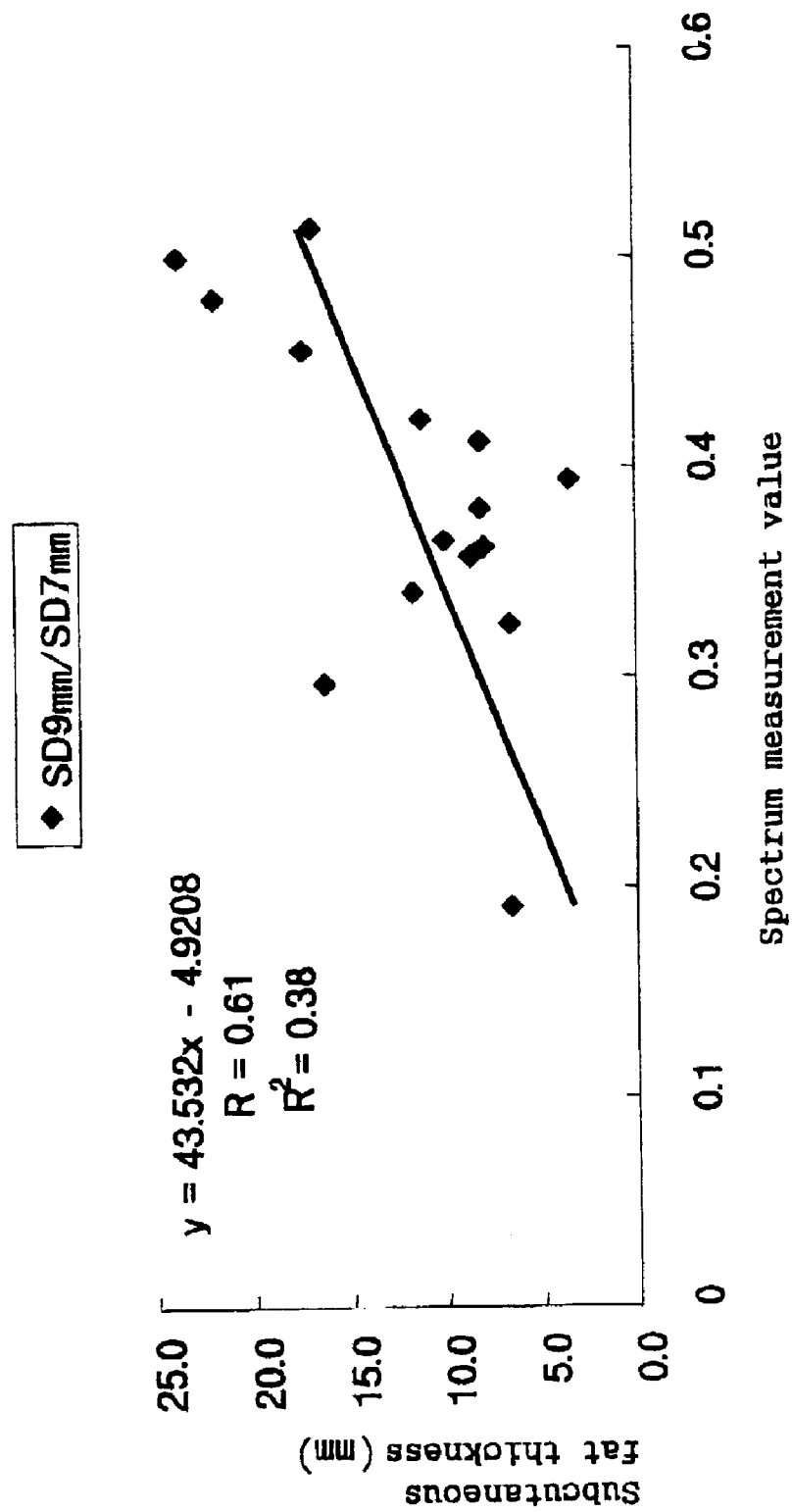
FIG. 17 is a graph showing living body data in the case of the present invention where the wavelength used is 950 nm.
Figure 18:
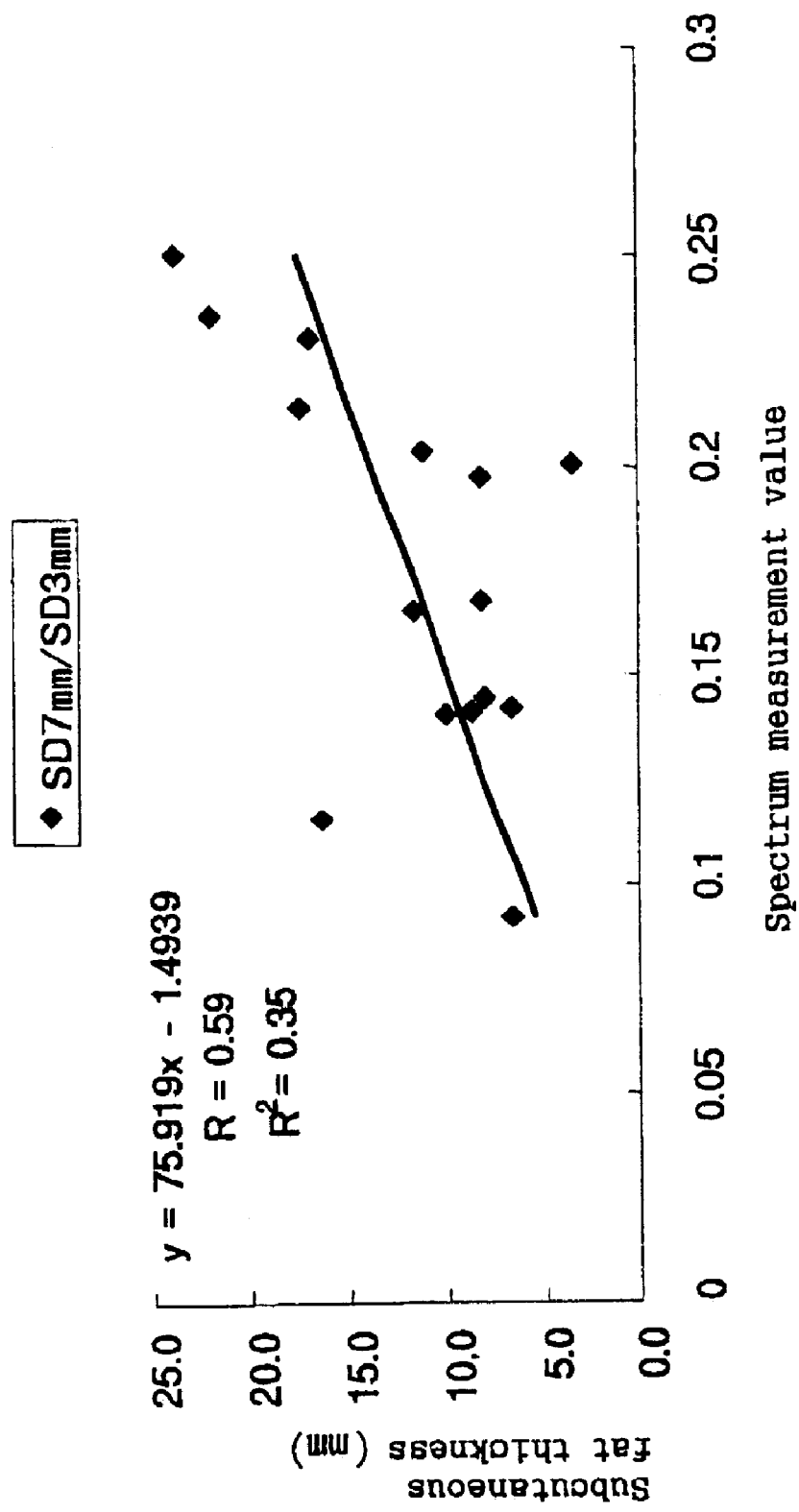
FIG. 18 is a graph showing living body data in the case of the present invention where the wavelength used is 950 nm.
Figure 19:
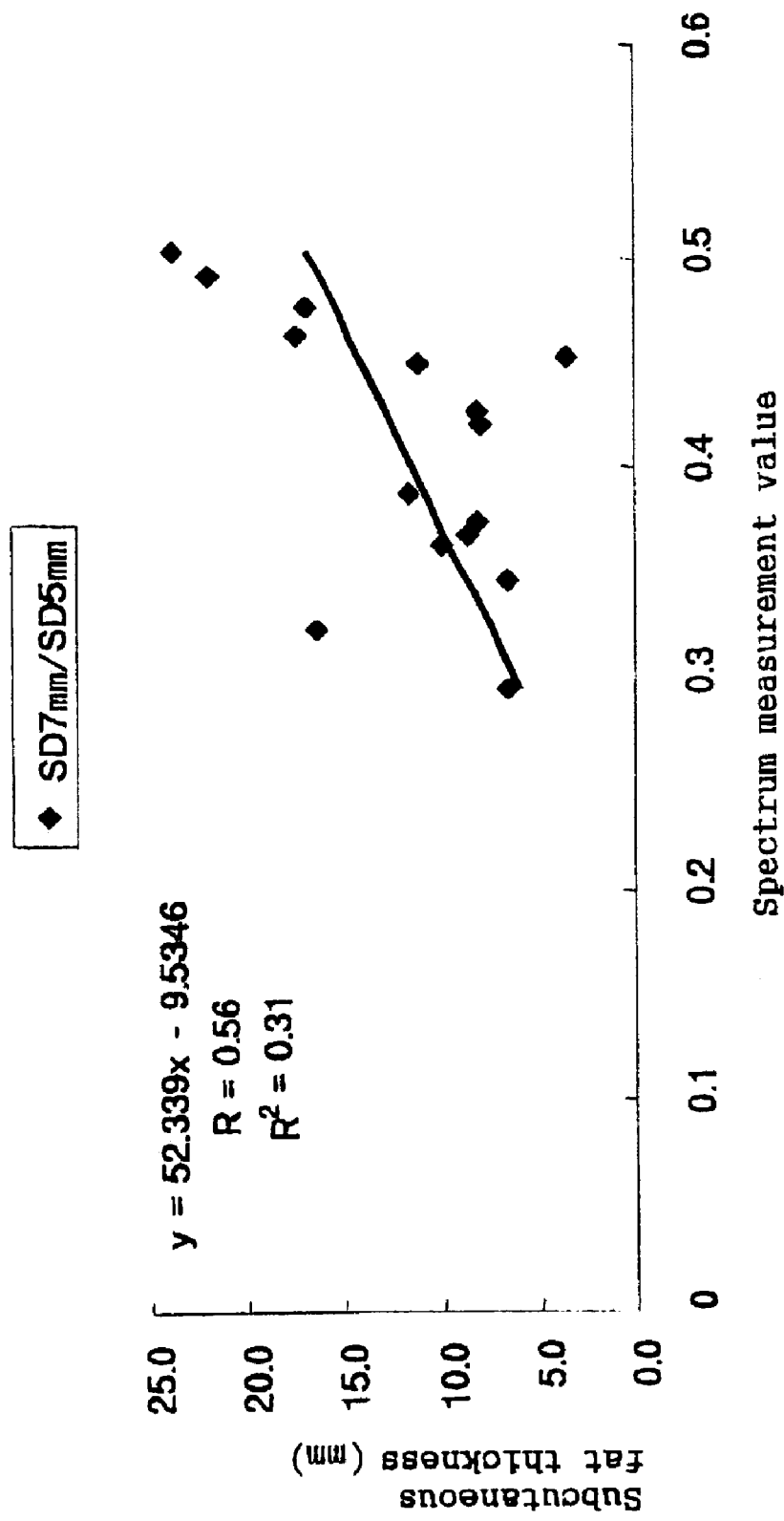
FIG. 19 is a graph showing living body data in the case of the present invention where the wavelength used is 950 nm.
Figure 20:
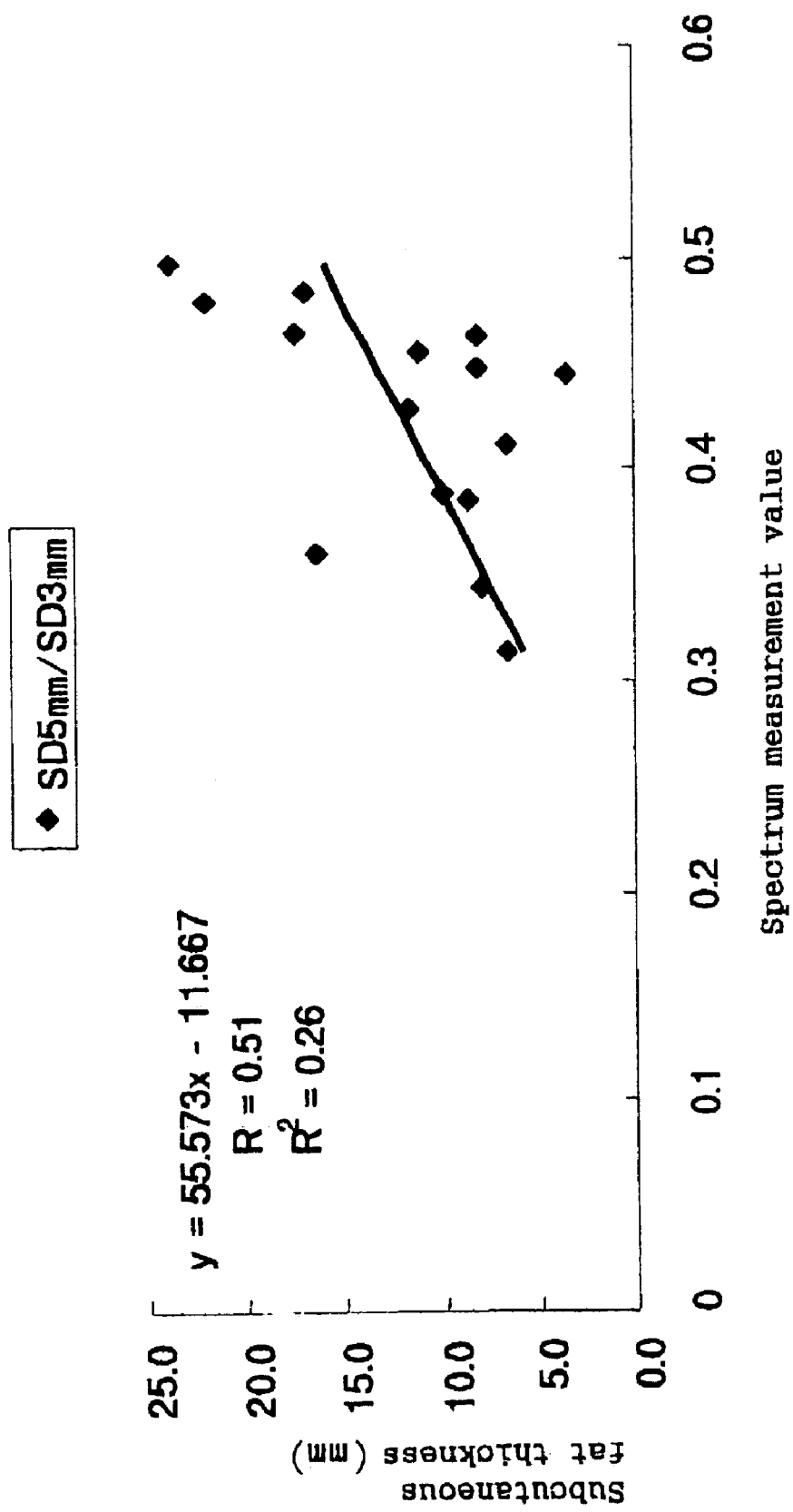
FIG. 20 is a graph showing living body data in the case of the present invention where the wavelength used is 950 nm.

The leftmost column of the uppermost table in FIG. 14 showing the cases of the present invention where the wavelength is 950 nm shows a case where the number of light receiving portions is two and the distance from the light emitting portion is 9 mm for the farther one and 3 mm for the closer one. The graph corresponding to the case is shown in FIG. 15. For the body fat thickness, the correlation expression is $y=125.48x+2.9141$, and the correlation coefficient R is $R=0.67$. In the case where the distances are 9 mm and 5 mm, the correlation coefficient R is $r=0.65$. In the case where the distances are 9 mm and 7 mm, the correlation coefficient R is $r=0.61$. The other columns show cases of 7 mm and 5 mm, 7 nm and 3 mm, and 5 mm and 3 mm, and the data are shown in a similar manner to the case of 9 mm.

As is apparent from this example, when the distance between the two light receiving portions exceeds 2 mm like in the present invention, the correlation coefficients are considerably more excellent than those of the conventional apparatus by correcting the output of the light receiving portion at a longer distance by the output of the light receiving portion at a shorter distance.

Figure 22:
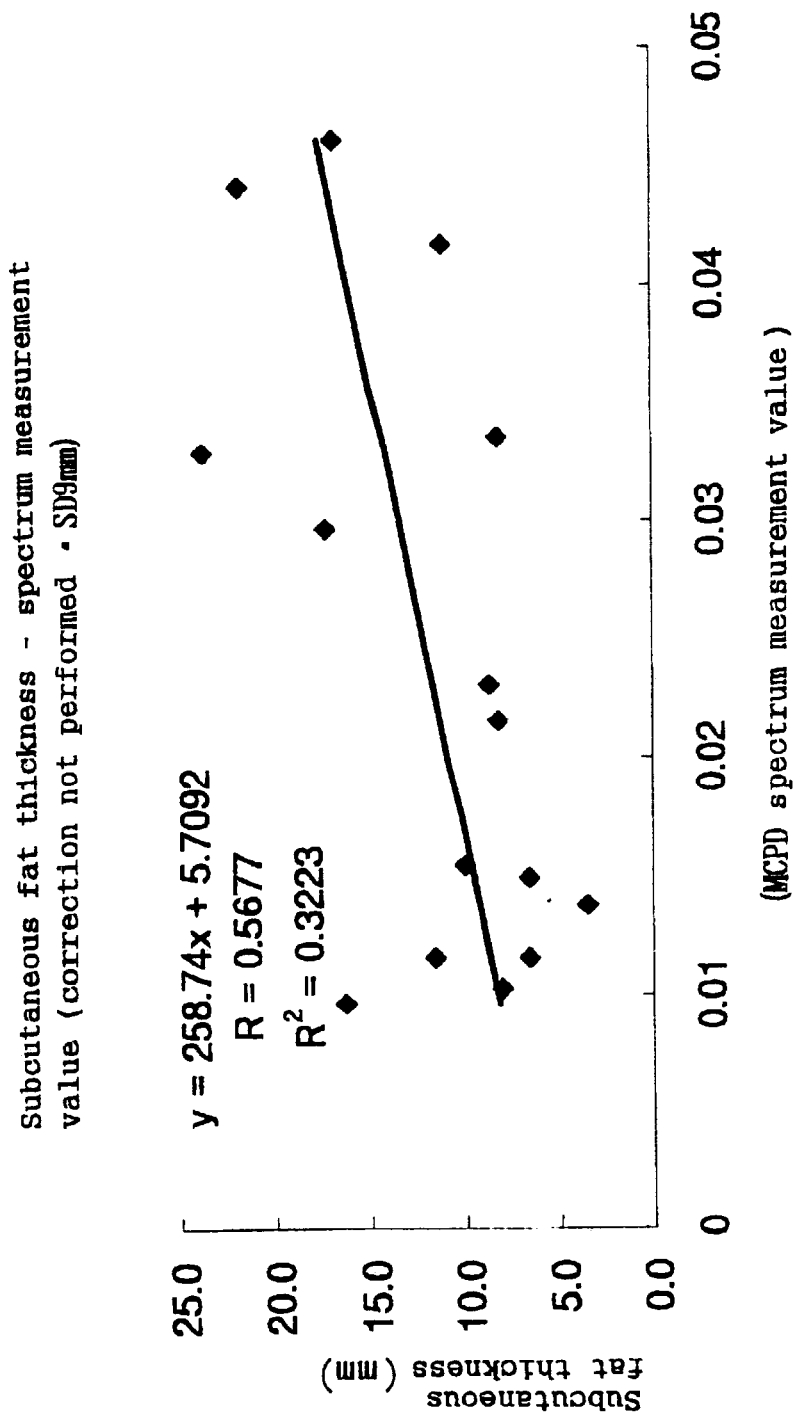
FIG. 22 is a graph showing living body data in the case, although not of the conventional apparatus, where processing is performed with one light receiving portion and the wavelength used is 650 nm.
Figure 23:
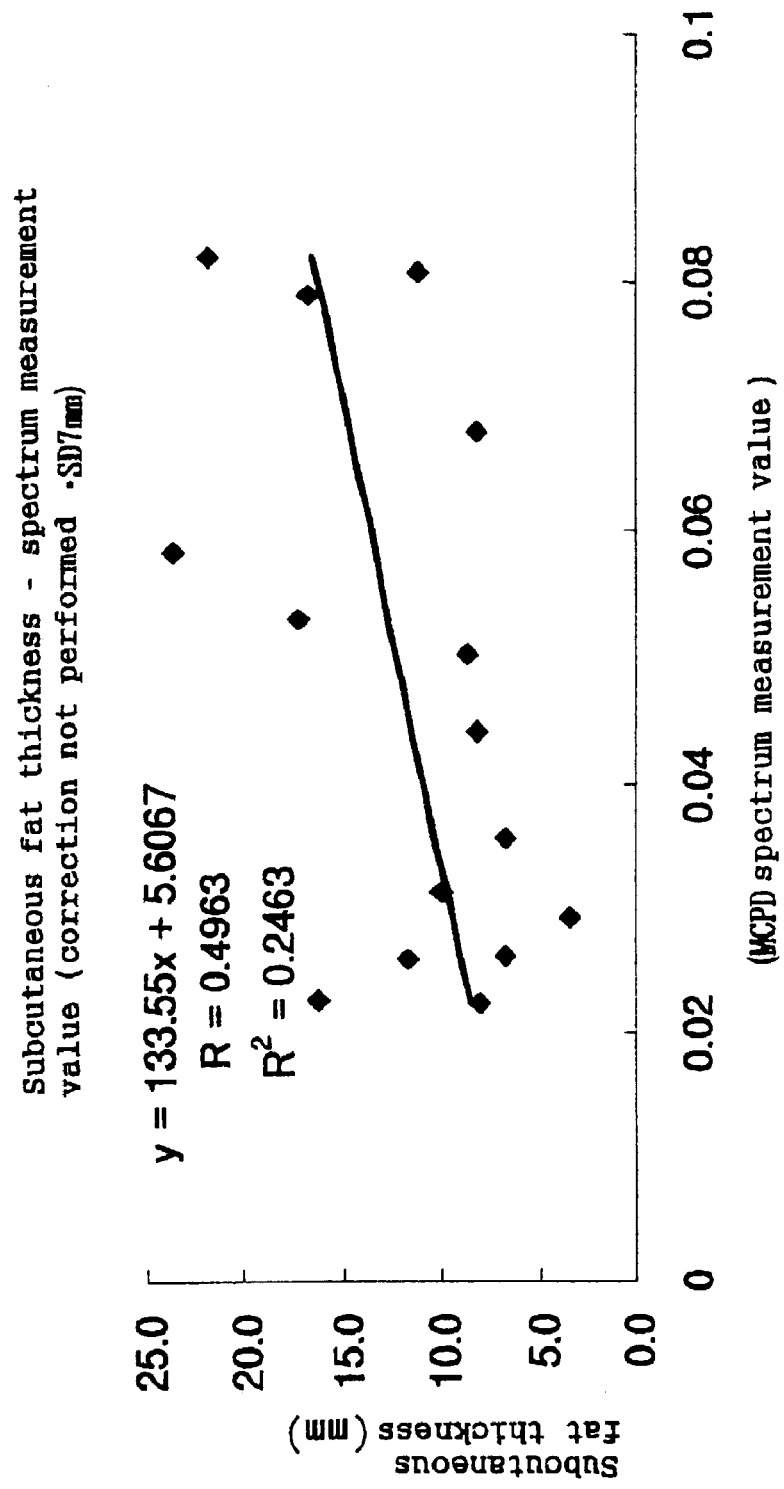
FIG. 23 is a graph showing living body data in the case, although not of the conventional apparatus, where processing is performed with one light receiving portion and the wavelength used is 650 nm.
Figure 24:
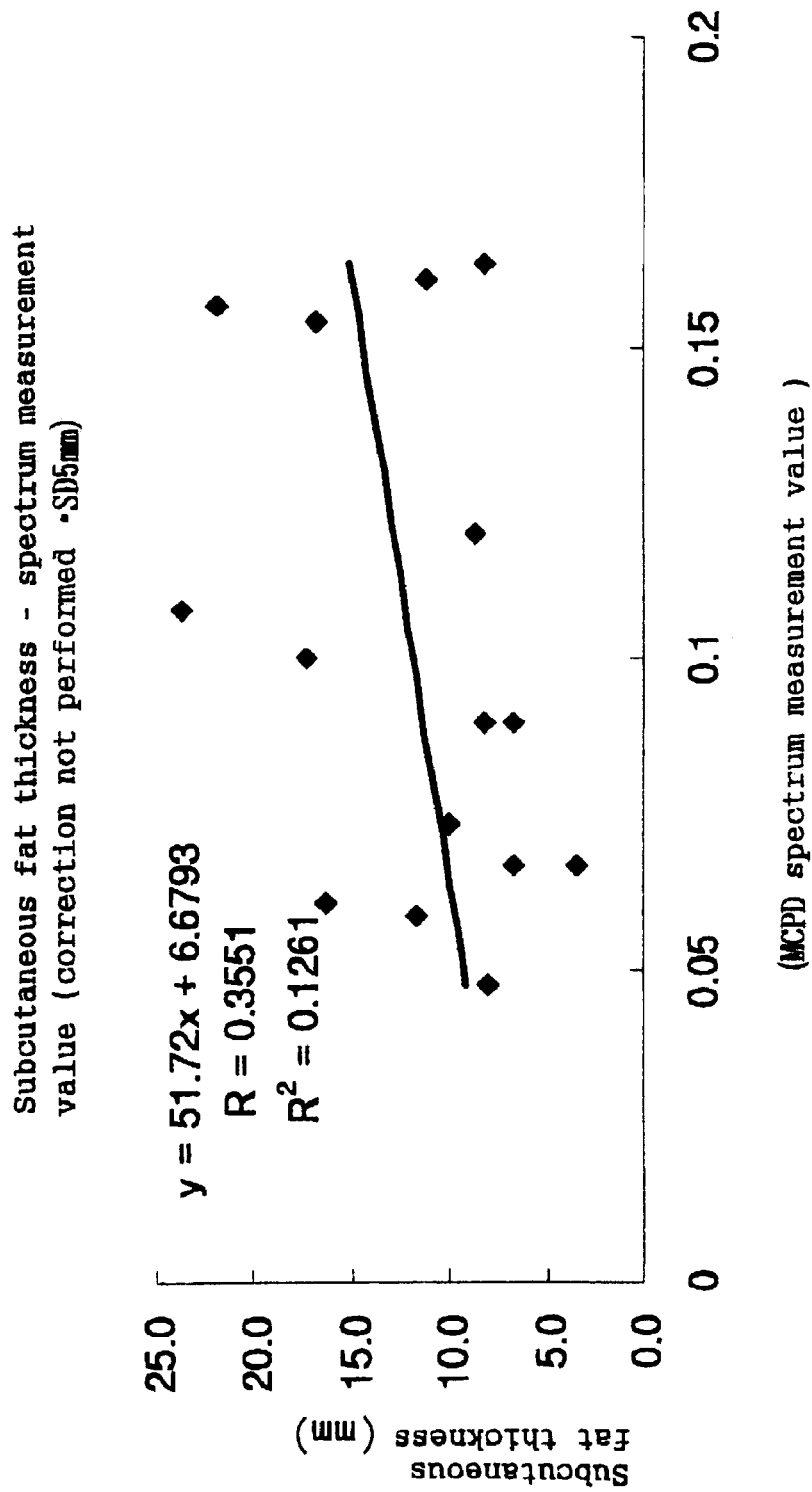
FIG. 24 is a graph showing living body data in the case, although not of the conventional apparatus, where processing is performed with one light receiving portion and the wavelength used is 650 nm.
Figure 25:
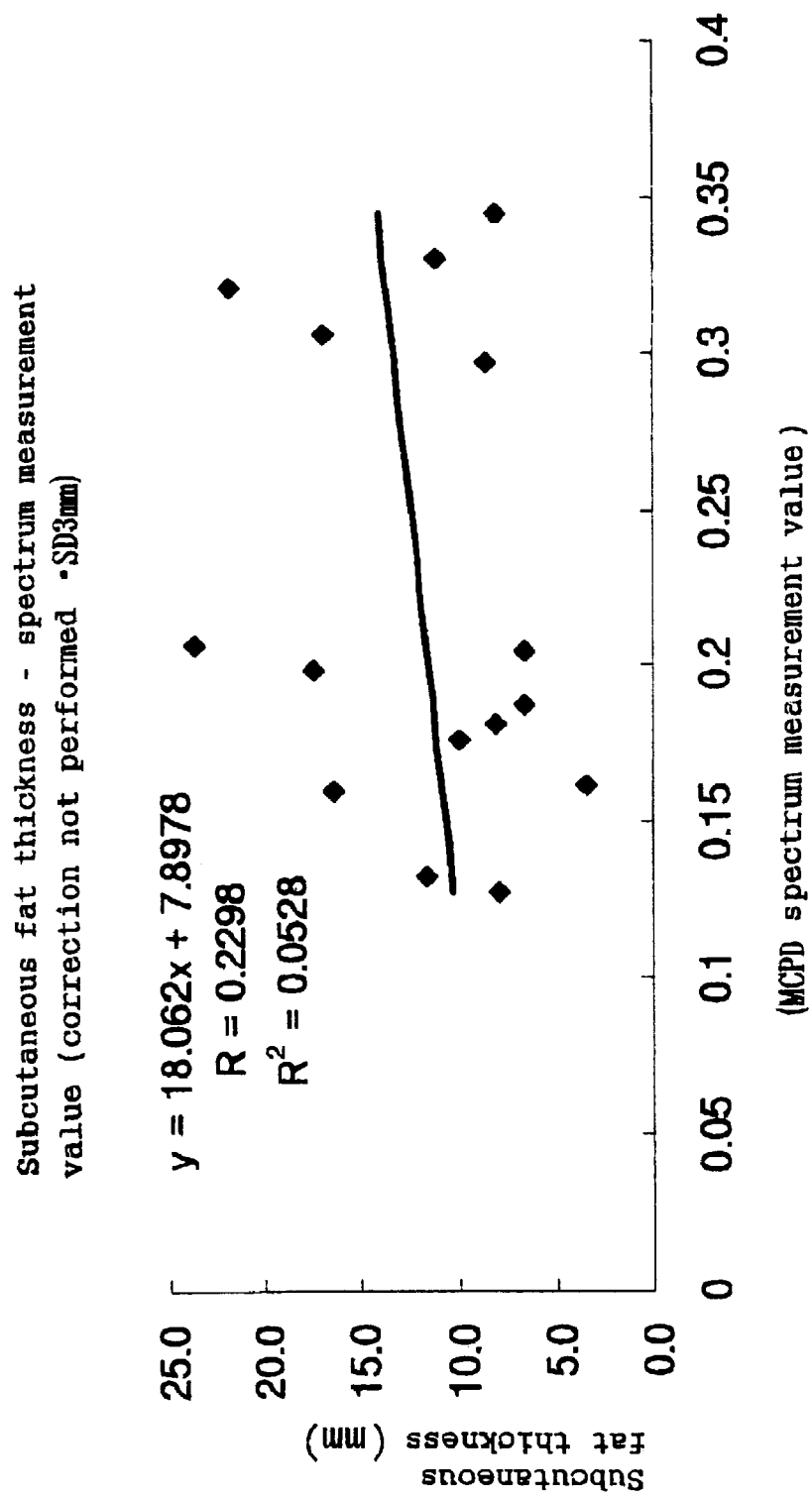
FIG. 25 is a graph showing living body data in the case, although not of the conventional apparatus, where processing is performed with one light receiving portion and the wavelength used is 650 nm.
Figure 26:
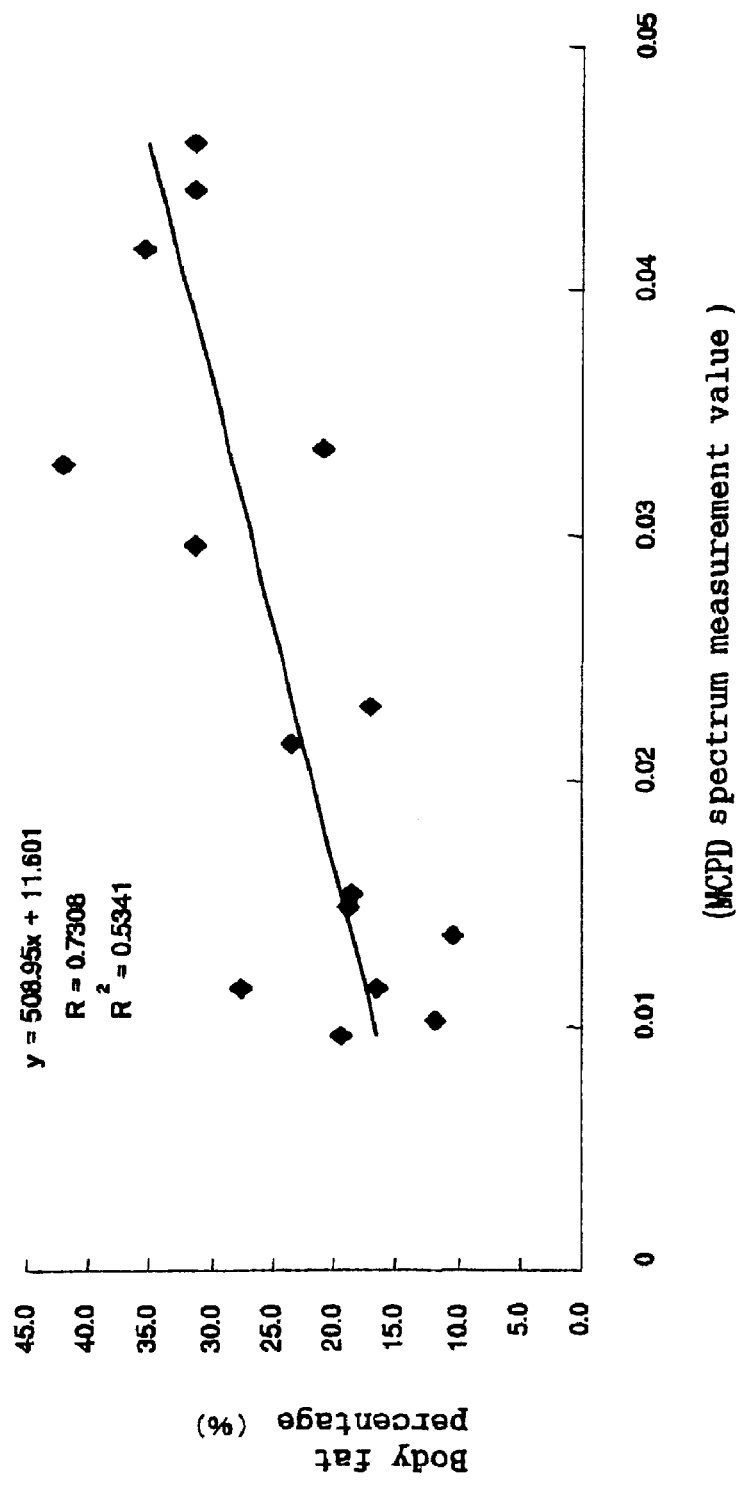
FIG. 26 is a graph showing living body data in the case, although not of the conventional apparatus, where processing is performed with one light receiving portion and the wavelength used is 650 nm.
Figure 27:
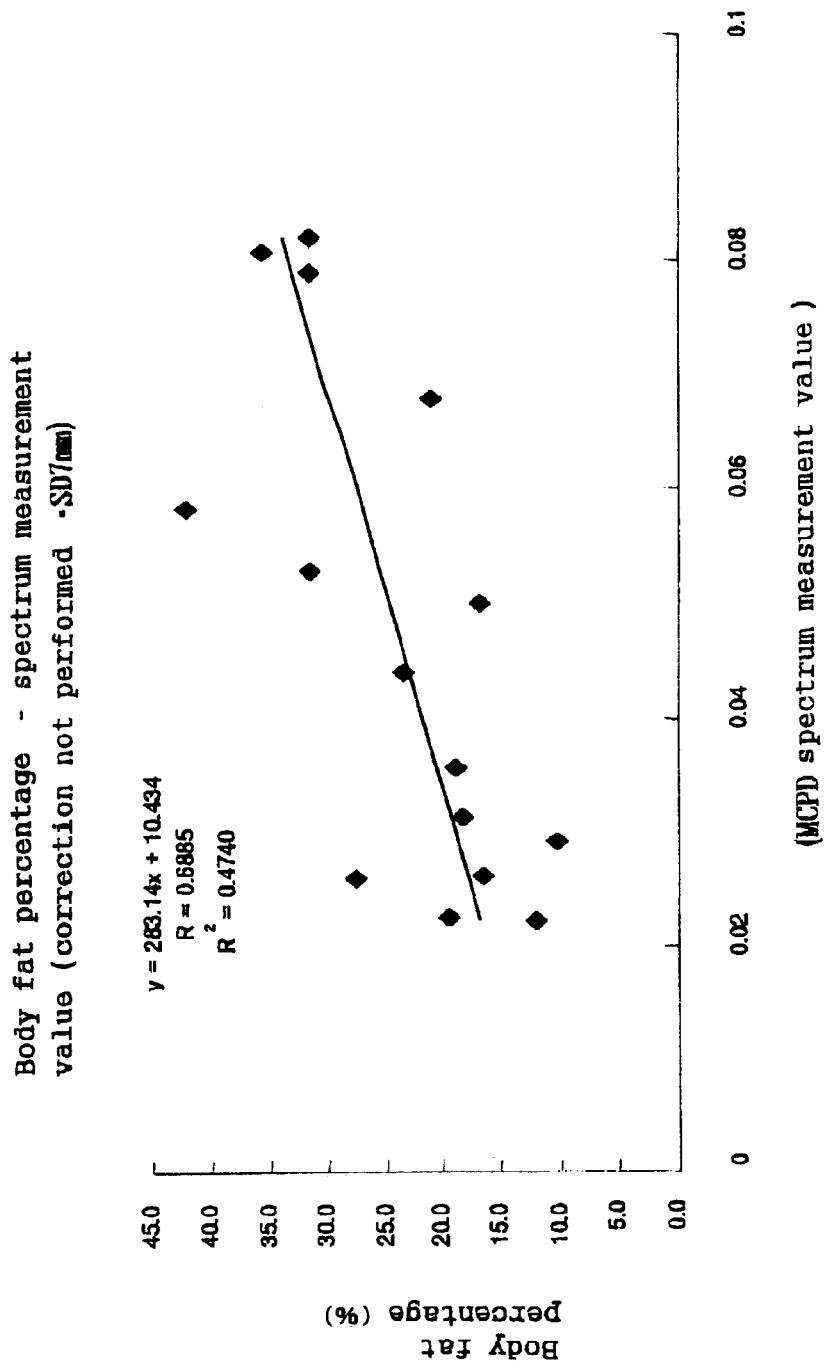
FIG. 27 is a graph showing living body data in the case, although not of the conventional apparatus, where processing is performed with one light receiving portion and the wavelength used is 650 nm.
Figure 28:
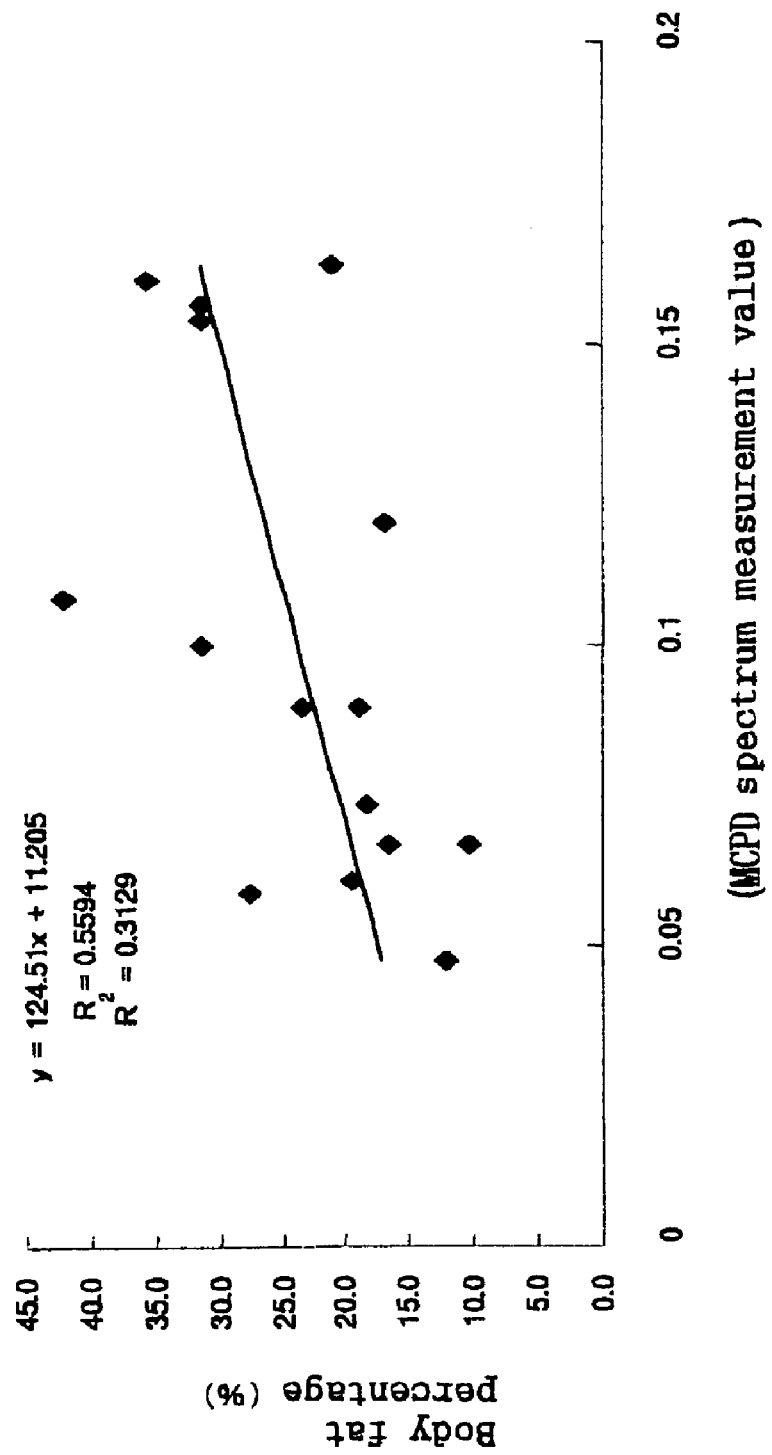
FIG. 28 is a graph showing living body data in the case, although not of the conventional apparatus, where processing is performed with one light receiving portion and the wavelength used is 650 nm.
Figure 29:
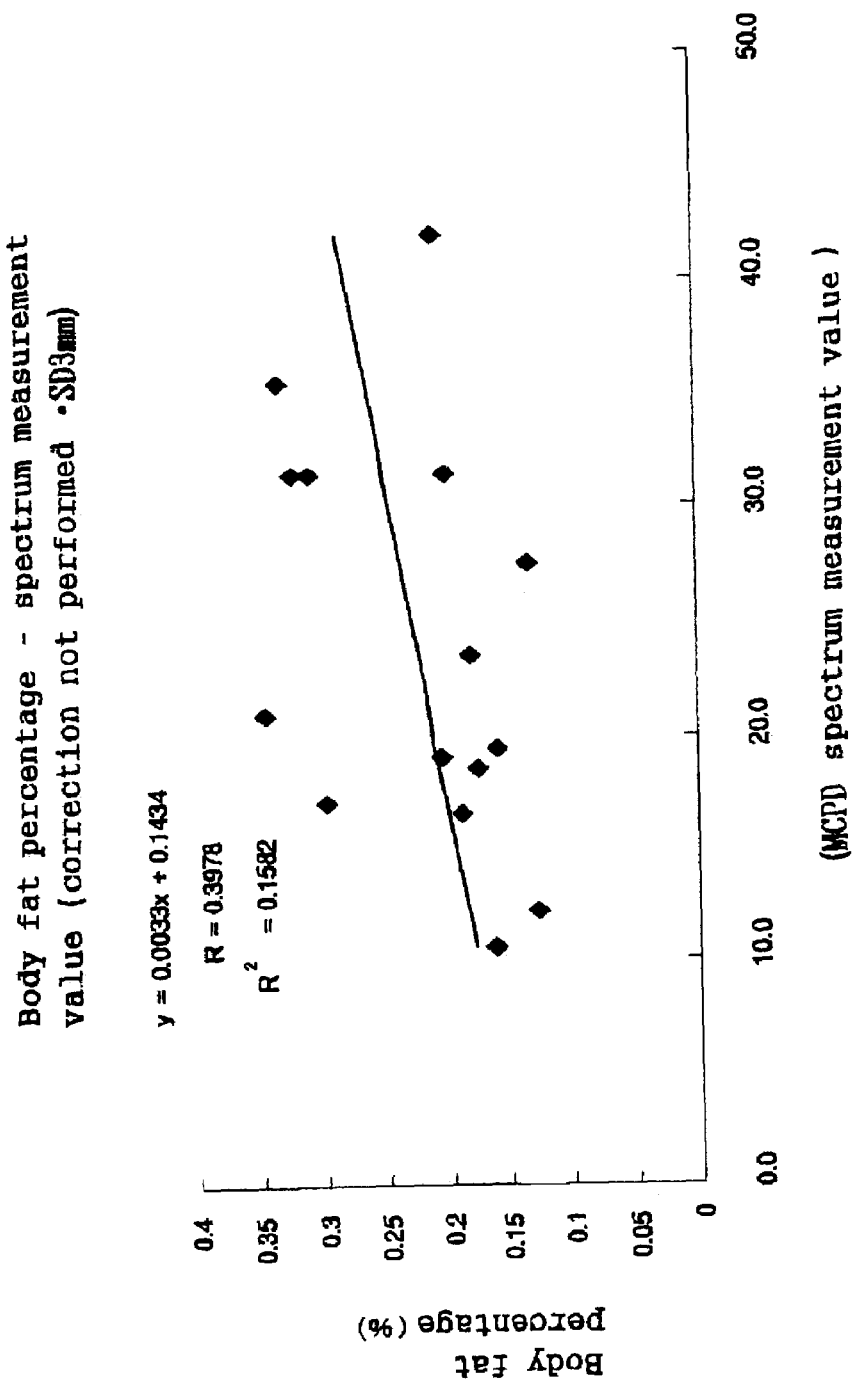
FIG. 29 is a graph showing living body data in the case, although not of the conventional apparatus, where processing is performed with one light receiving portion and the wavelength used is 650 nm.

The leftmost column in FIG. 21 showing the cases where the number of light receiving portions is one and the wavelength is 650 nm shows a case where the number of light receiving portions is one and the light receiving portion is situated 9 mm away from the light emitting portion. The graphs corresponding to the case are shown in FIG. 22 (body fat thickness) and FIG. 26 (body fat percentage). For the body fat thickness of FIG. 22, the correlation expression is $y=258.74x+5.70952$, and the correlation coefficient R is $R=0.5677$. For the body fat percentage of FIG. 26, the correlation expression is $y=508.95x+11.601$, and the correlation coefficient R is $R=0.7308$. The other columns show cases of the distances of 7 mm, 5 mm and 3 mm, and the data are shown in a similar manner to the case of 9 mm.

The leftmost column of the uppermost table in FIG. 30 showing the cases of the present invention where the wavelength is 650 nm shows a case where the number of light receiving portions is two and the distance from the light emitting portion is 9 mm for the farther one and 3 mm for the closer one. The graphs corresponding to the case are shown in FIGS. 31 and 37.

Figure 31:
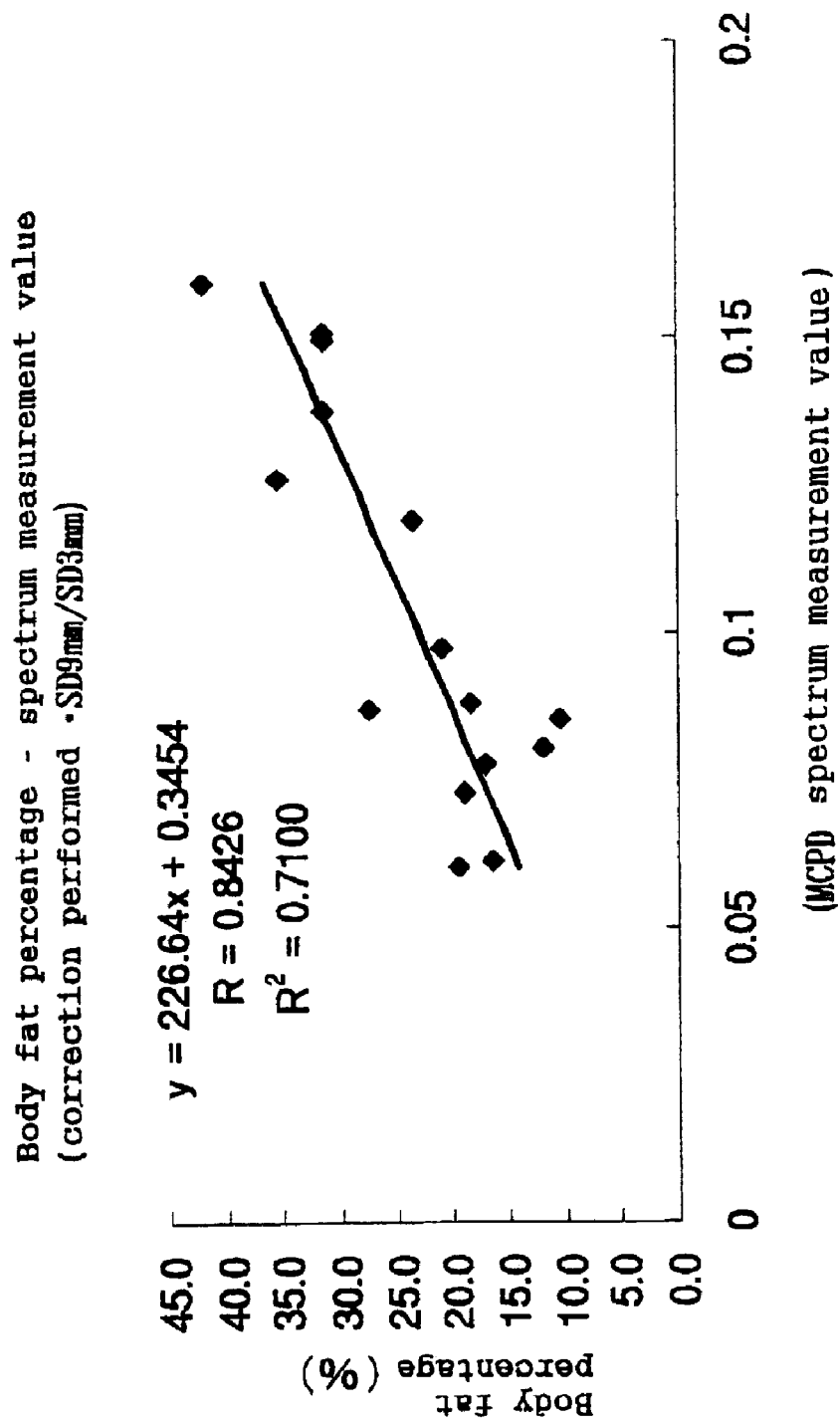
FIG. 31 is a graph showing living body data in the case of the present invention where the wavelength used is 650 nm.
Figure 32:
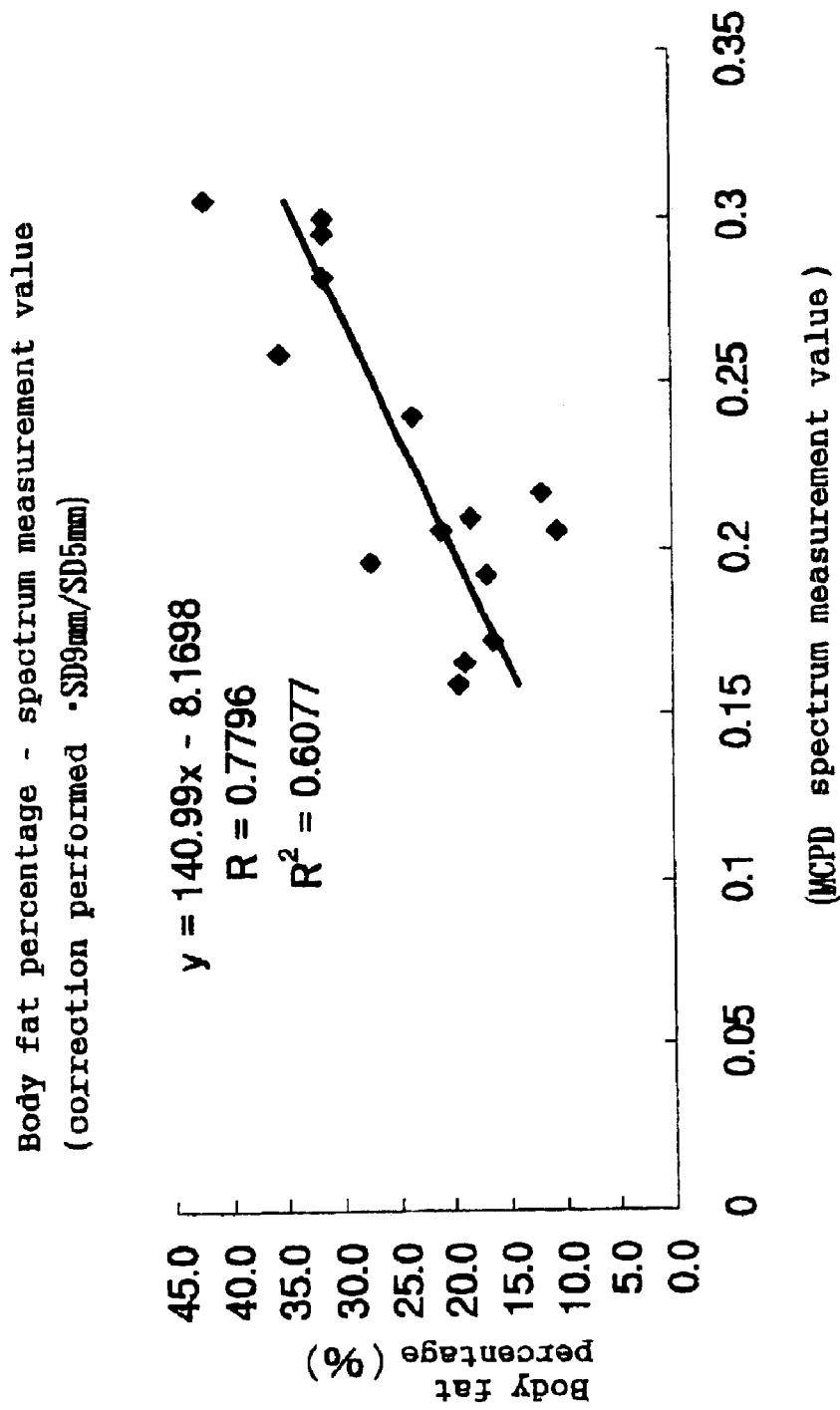
FIG. 32 is a graph showing living body data in the case of the present invention where the wavelength used is 650 nm.
Figure 33:
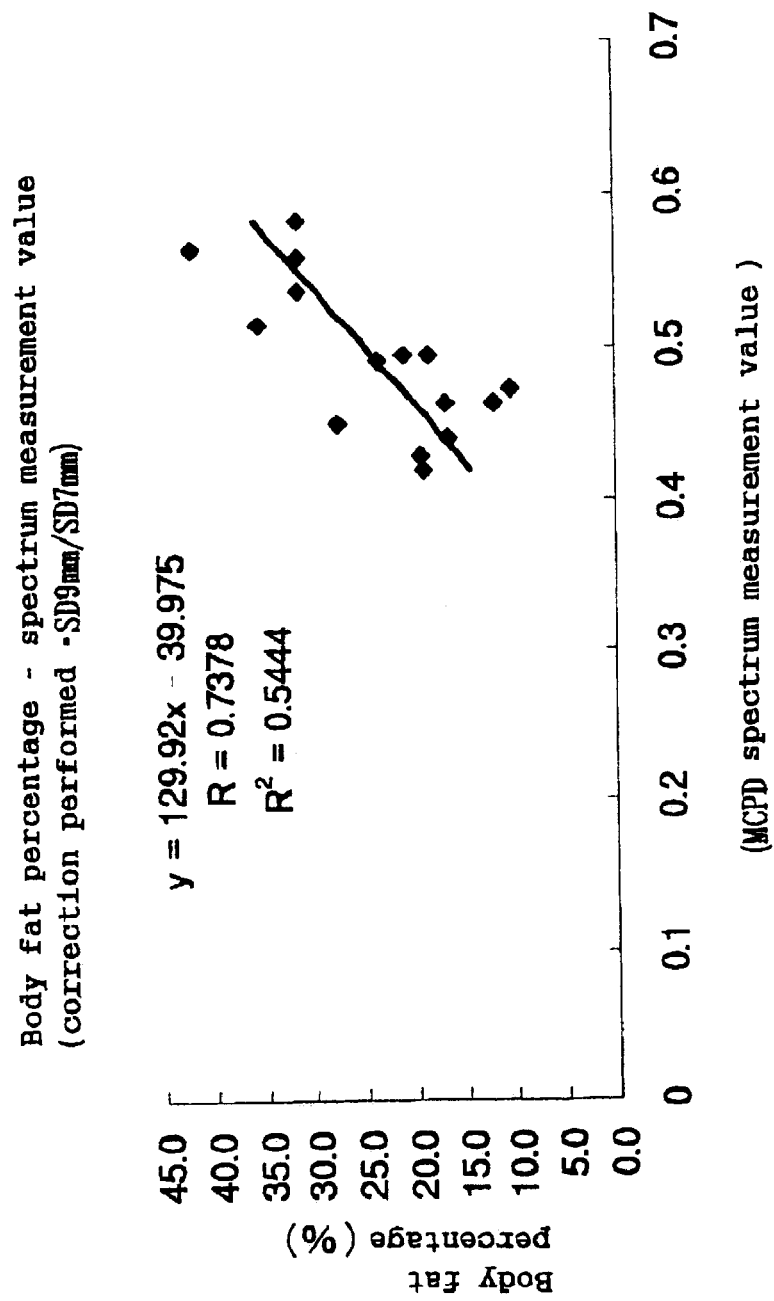
FIG. 33 is a graph showing living body data in the case of the present invention where the wavelength used is 650 nm.
Figure 34:
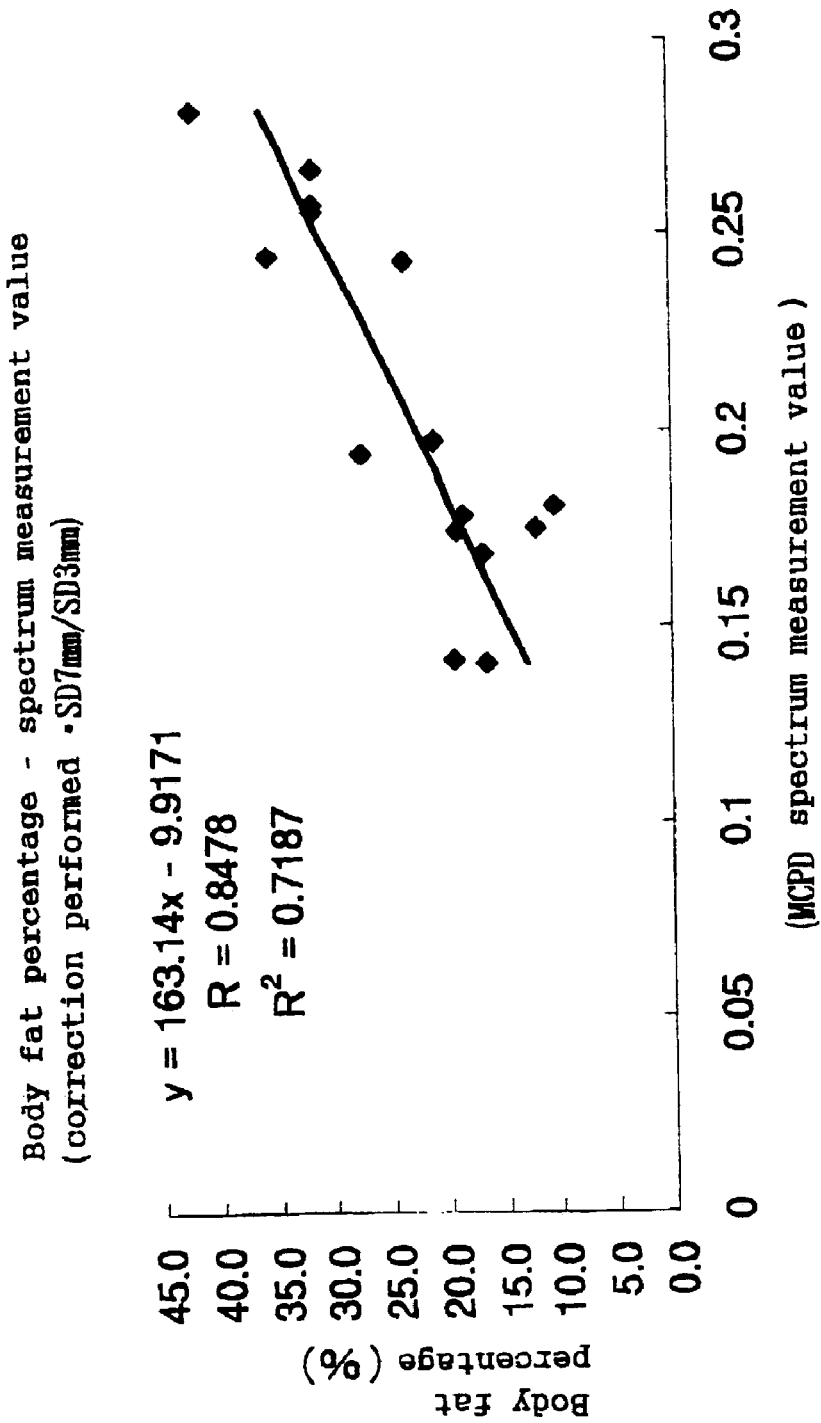
FIG. 34 is a graph showing living body data in the case of the present invention where the wavelength used is 650 nm.
Figure 35:
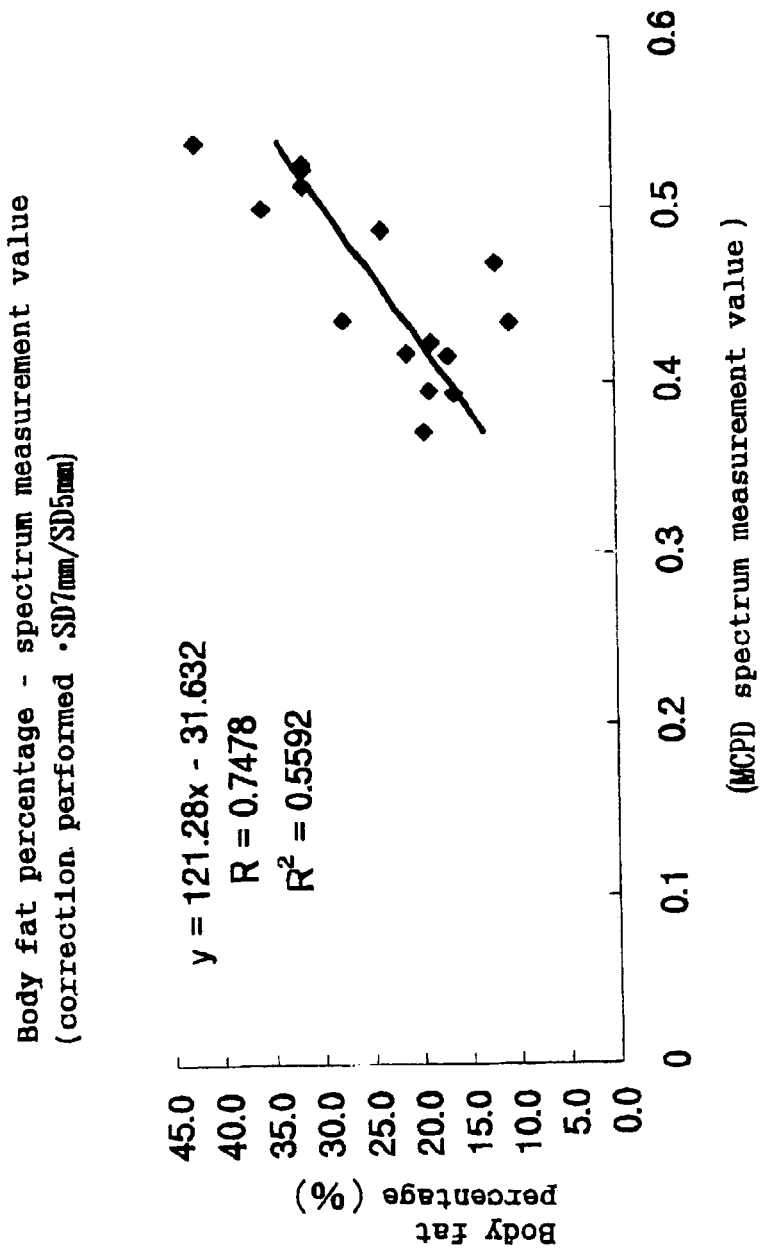
FIG. 35 is a graph showing living body data in the case of the present invention where the wavelength used is 650 nm.
Figure 36:
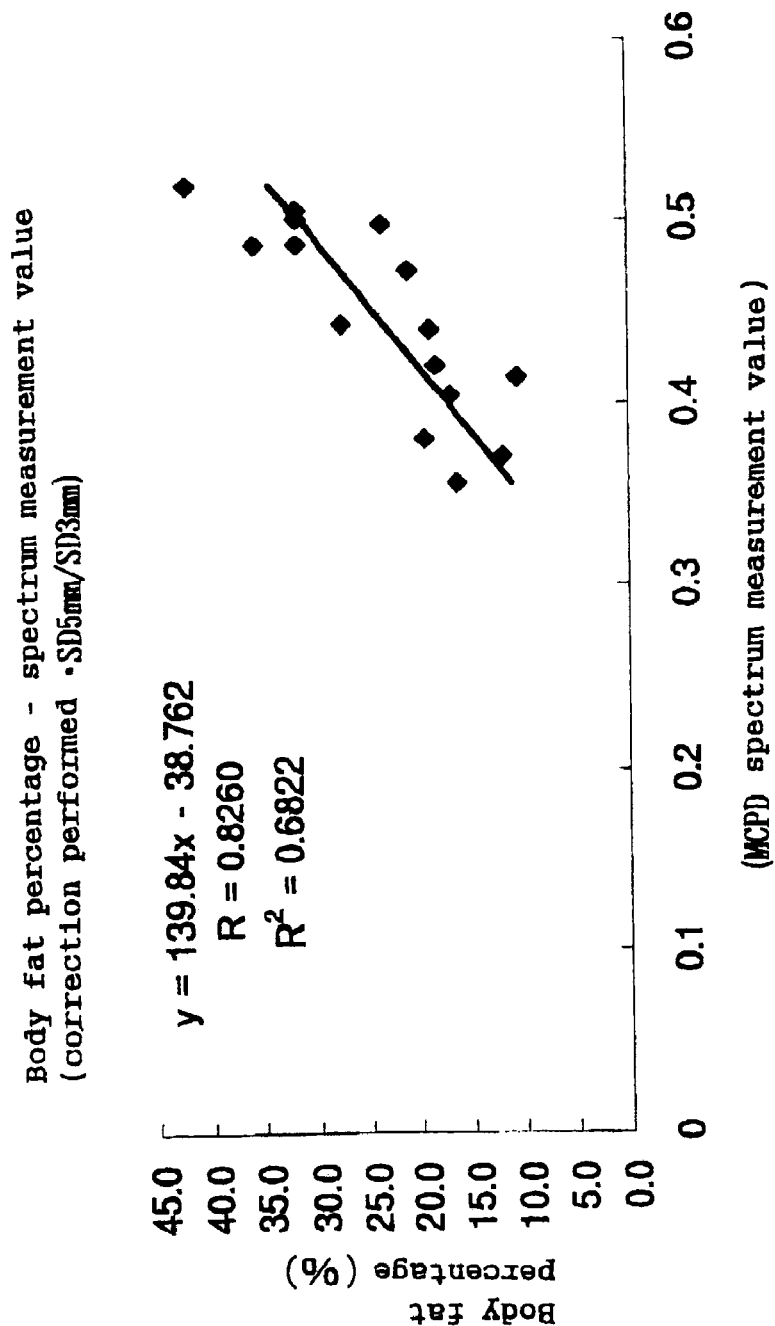
FIG. 36 is a graph showing living body data in the case of the present invention where the wavelength used is 650 nm.

For the body fat percentage of FIG. 31, the correlation expression is $y=226.64x+0.3454$, and the correlation coefficient R is $R=0.8426$. In the case where the distances are 9 mm and 5 mm, the correlation coefficient R is $r=0.7796$. In the case where the distances are 9 mm and 7 mm, the correlation coefficient R is $r=0.7378$. The other columns show cases of 7 mm and 5 mm, 7 mm and 3 mm, and 5 mm and 3 mm, and the data are displayed in a similar manner to the case of 9 mm.

Figure 37:
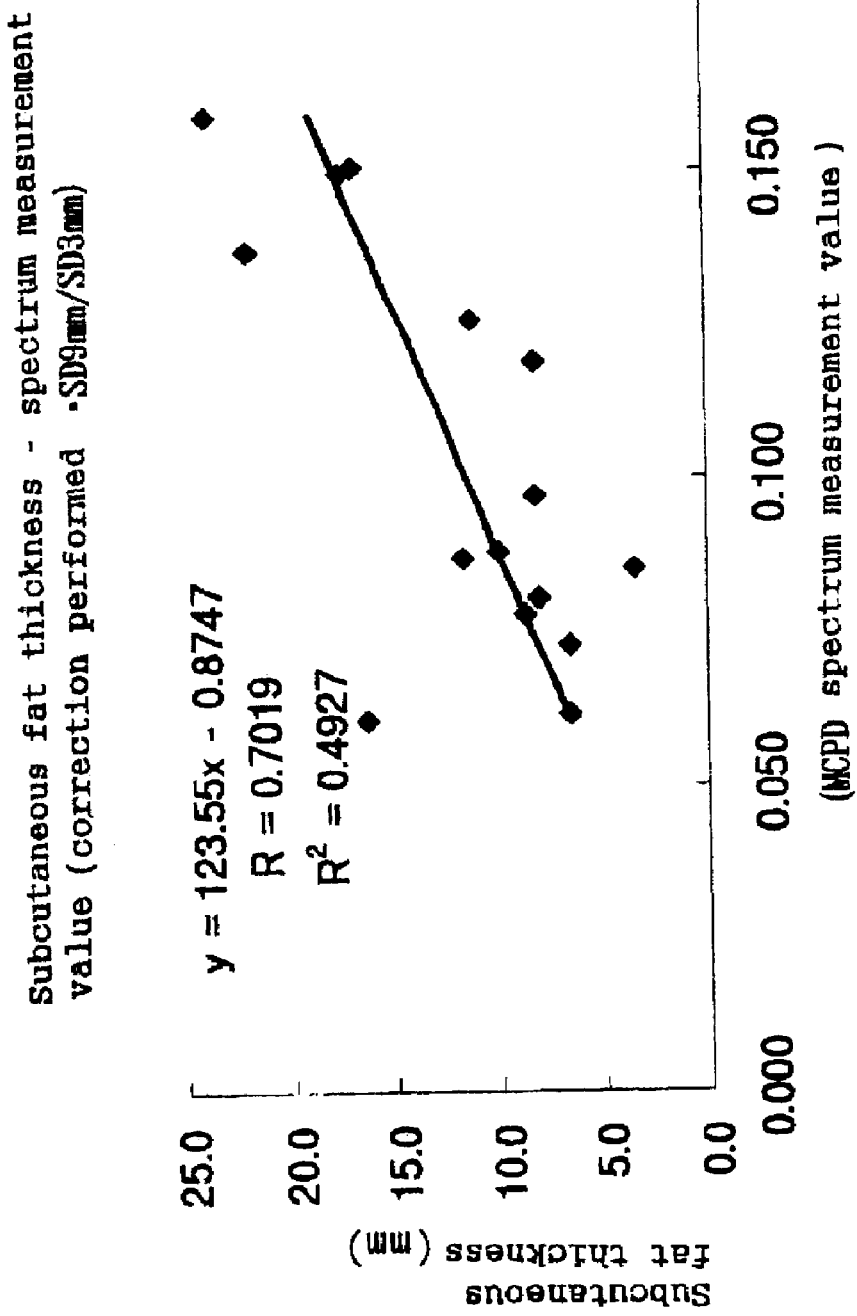
FIG. 37 is a graph showing living body data in the case of the present invention where the wavelength used is 650 nm.
Figure 38:
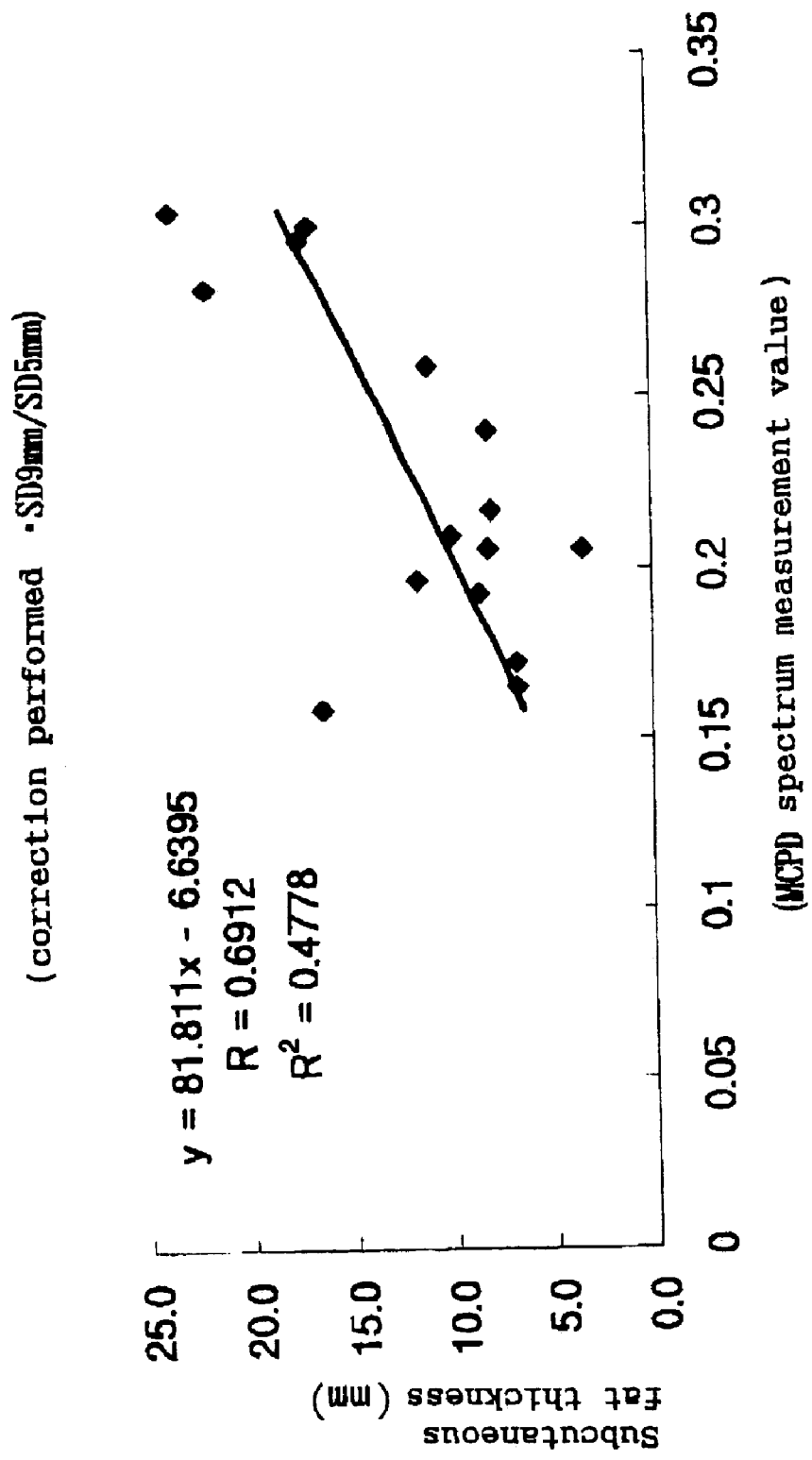
FIG. 38 is a graph showing living body data in the case of the present invention where the wavelength used is 650 nm.
Figure 39:
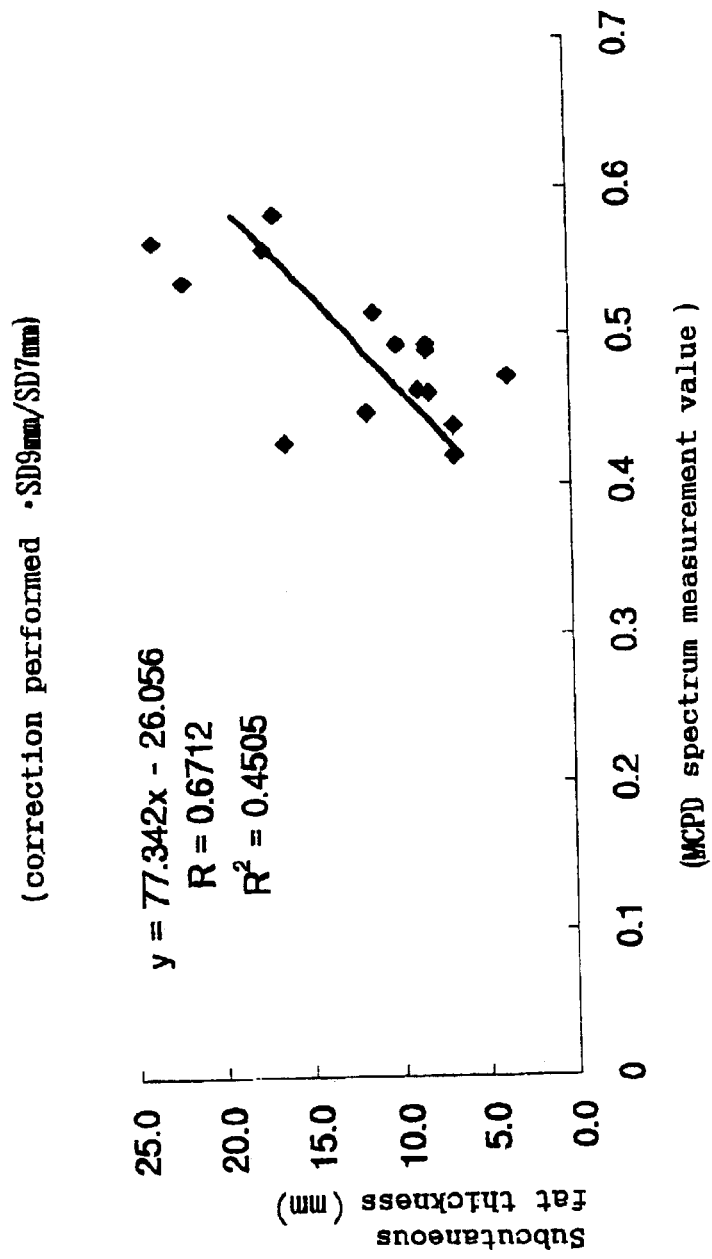
FIG. 39 is a graph showing living body data in the case of the present invention where the wavelength used is 650 nm.
Figure 40:
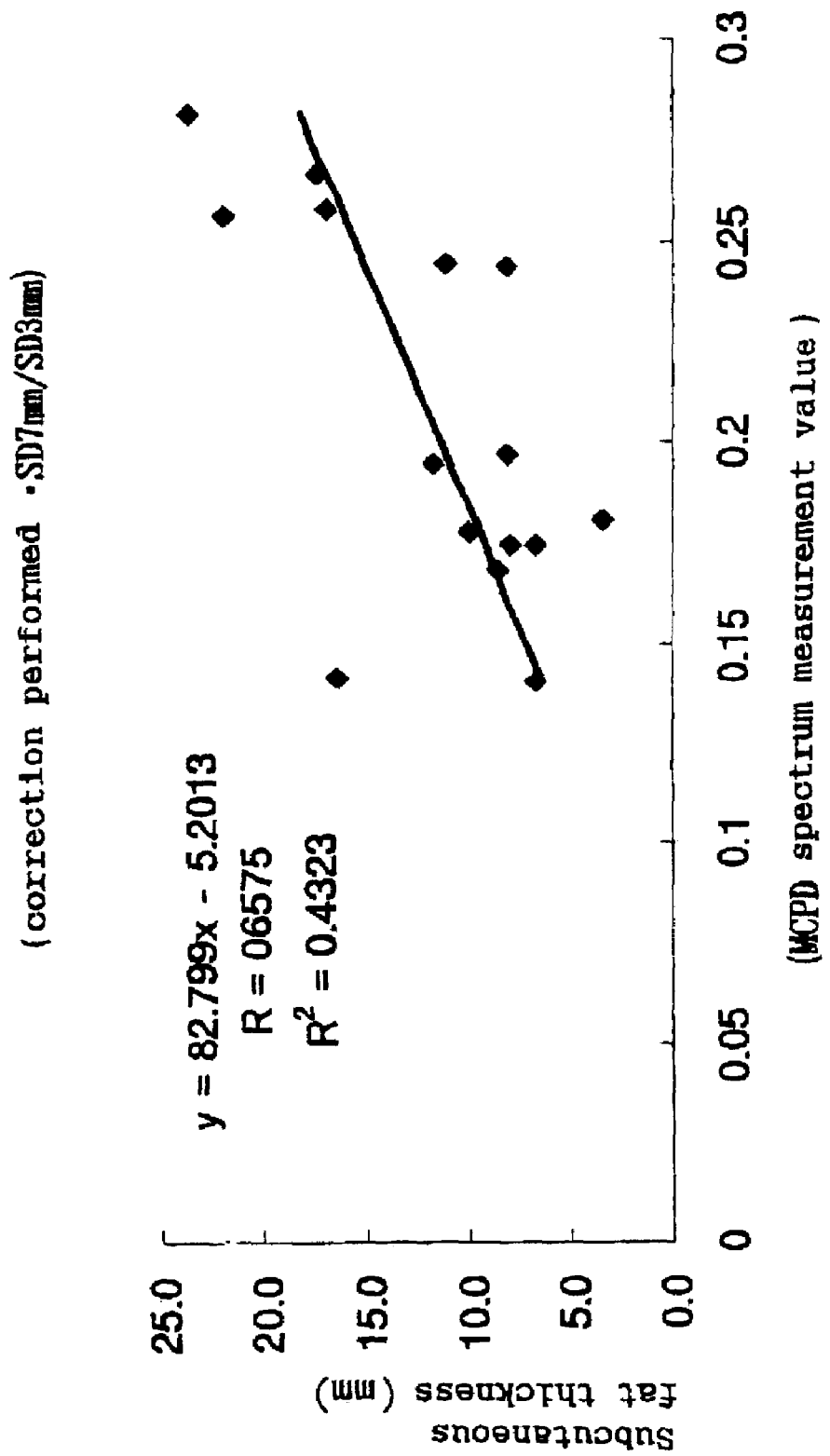
FIG. 40 is a graph showing living body data in the case of the present invention where the wavelength used is 650 nm.
Figure 41:
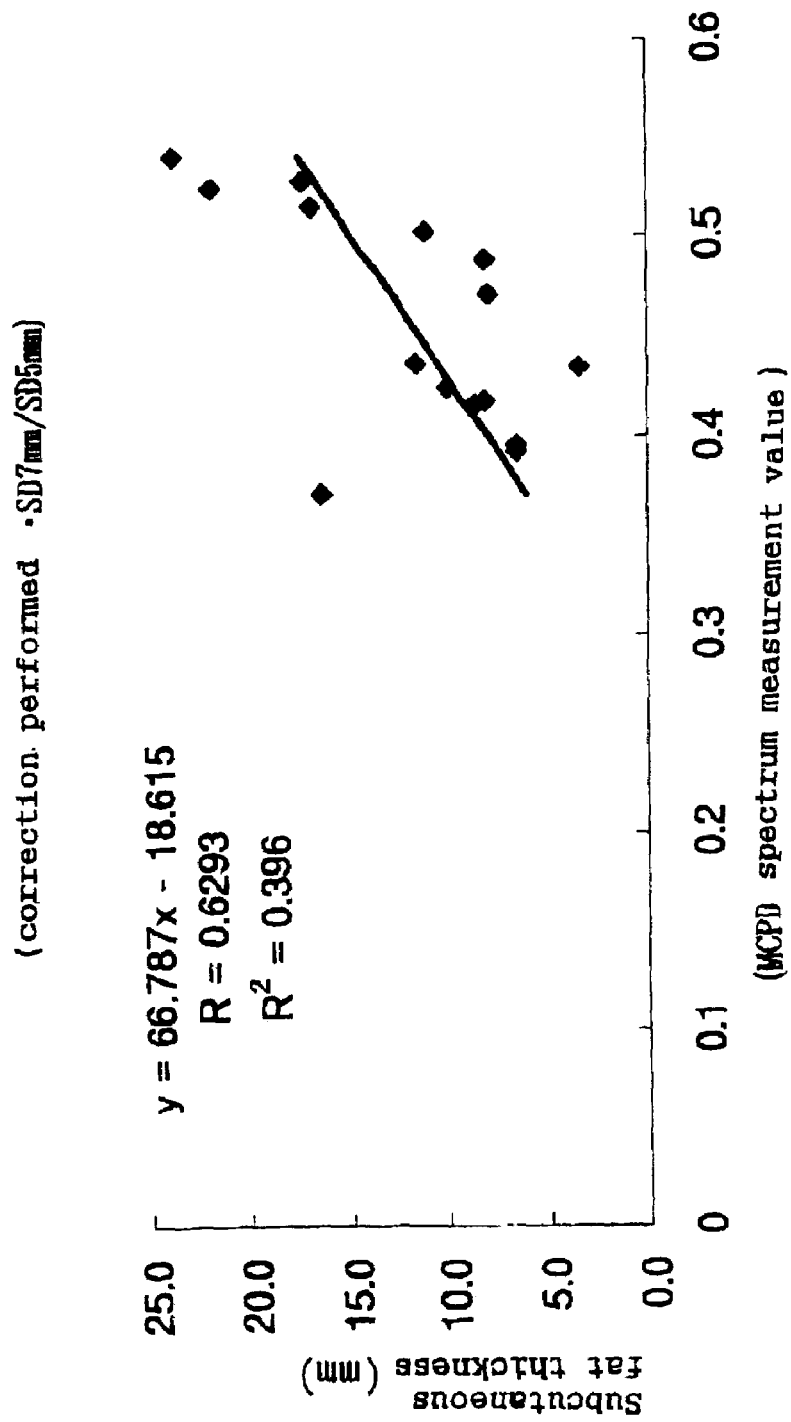
FIG. 41 is a graph showing living body data in the case of the present invention where the wavelength used is 650 nm.
Figure 42:
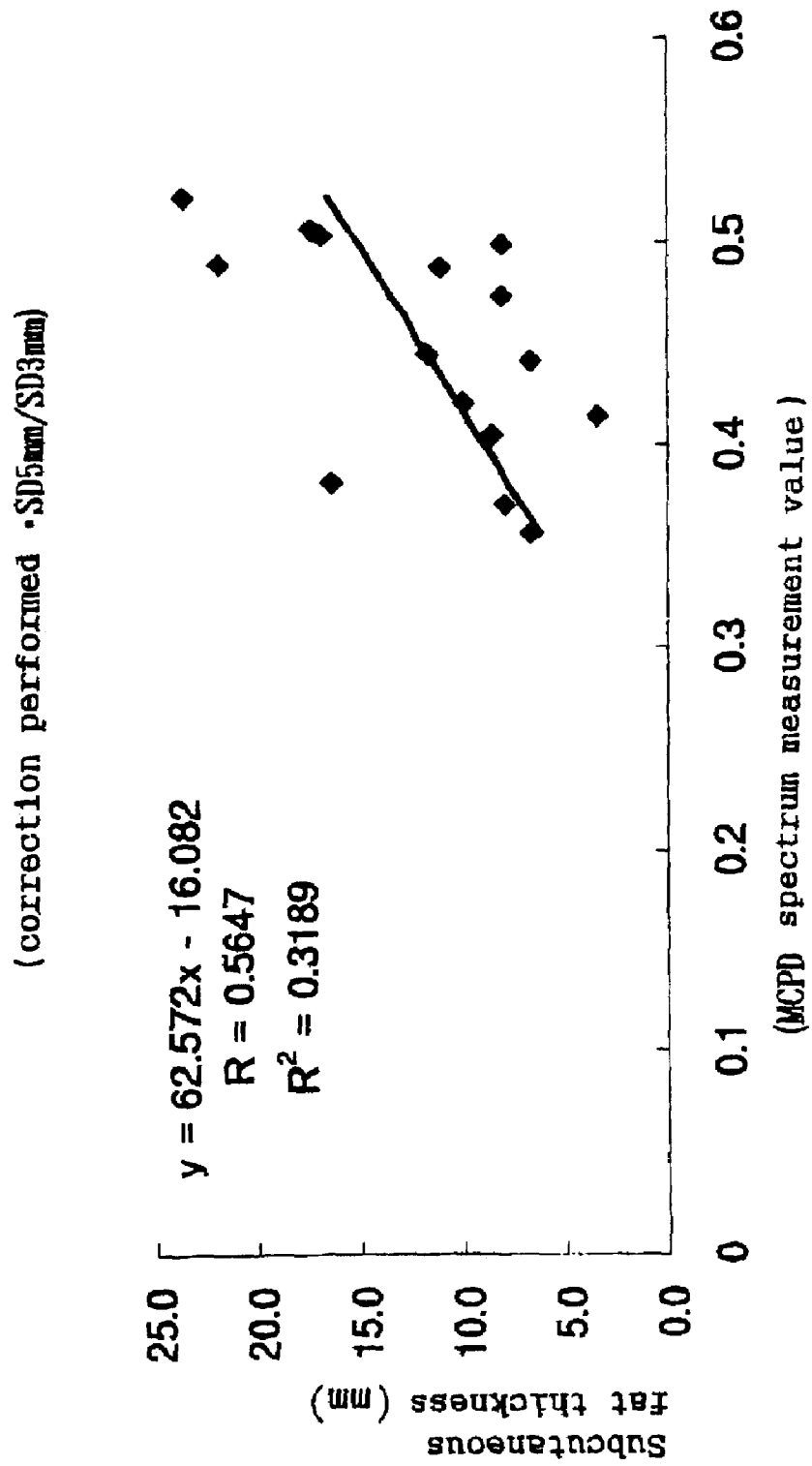
FIG. 42 is a graph showing living body data in the case of the present invention where the wavelength used is 650 nm.

For the body fat thickness of FIG. 37, the correlation expression is $y=123.55x-0.8747$, and the correlation coefficient R is $R=0.7019$. In the case where the distances are 9 mm and 5 mm, the correlation coefficient R is $r=0.6912$. In the case where the distances are 9 mm and 7 mm, the correlation coefficient R is $r=0.6712$. The other columns show cases of 7 mm and 5 mm, 7 mm and 3 mm, and 5 mm and 3 mm, and the data are displayed in a similar manner to the case of 9 mm.

As is apparent from this example, in the case of 650 nm, when the distance between the two light receiving portions exceeds 2 mm like in the present invention, for both the body fat percentage and the body fat thickness, the correlation coefficients are considerably more excellent than those of the conventional apparatus by correcting the output of the light receiving portion at a longer distance by the output of the light receiving portion at a shorter distance.

Further, in the cases where light of a wavelength of 650 nm is used, since the living body transmittance is inferior, even when a disturbance such as sunlight is present, the 650-nm wavelength of sunlight does not readily intrude into the living body, so that noise is suppressed to be low. However, light of a wavelength shorter than 600 nm cannot be used because a necessary quantity of light can not transmit through the living body. A wavelength of approximately 650 nm is most suitable. Therefore, it is desirable to perform the measurement by use of all or some of the wavelength components among 600 nm and 660 nm.

It is considered that the correlation is susceptible to improvement even when the light receiving device 4B is situated at a distance of 9 mm or more. However, this is not practical because attenuation of a quantity of the light is large.

From these test data, it can be said that both the body fat percentage and the body fat thickness can be more accurately measured when the distance is not more than 3 mm for the closer light receiving portion and not more than 9 mm for the farther light receiving portion.

Therefore, the above means that dividing the detection value obtained by detecting the light having propagated through a deep part of a living body by the detection value of the light having propagated through the surface of the living body produces an effect of correcting an individual difference in the surface configuration of the living body, that is, a difference in skin color.

For the division of the second light quantity by the first light quantity, various approximate expressions were examined, and it was found experimentaly that simply dividing is most effective as mentioned above. This fact is practically very effective because the electric circuit for calculating the body fat amount or the body fat thickness can be simplified.

In this embodiment, since two light receiving portions are provided, the following effect is also produced: When the apparatus is not completely in contact with the living body, the values detected by the two light receiving portions both change in the structure of the present invention although the value significantly deviates when only one light receiving portion is provided. Even if the apparatus is not completely in contact with the living body and the light reception quantity uniformly decreases, since one of the values is divided by the other value to calculate the body fat percentage or the body fat thickness, deviation is suppressed. This fact is can be said to be effective because a practical effect that the measurement accuracy is improved is produced.

In this embodiment, light with a central wavelength of 650 nm is used, and this produces an effect of suppressing the influence of disturbance light because the transmittance at which this light is transmitted by the living body is lower than that of near infrared rays of a wavelength in the vicinity of approximately 950 nm. That is, even if disturbance light having various wavelengths is present, since visible light largely attenuates before it reaches the light receiving portions, in comparison with the case of near infrared rays accurate measurement can be performed.

Further the amount of the penetration of the infrared ray having about 950 nm wavelength changes largely at the position of the fat where there is absorbing peak and then the amount is effected from the quality of fat.

Specially when the devices are fixed to the skin, and the quality of the fat is different for the subjective persons, the detected value does not have precision.

When the present invention uses visible wavelength which is hard to be effected with absorbing property of fat, the fat thickness and body fat percentage can be precisely detected.

The preferable wavelength has such wavelength that is less absorbed by fat and the visible light is preferable, especially the 600 nm to 660 nm.

Then the present invention has superior detection precision which is less effected from the difference of the quality of fat in the persons.

As described above, according to the body fat detecting apparatus of this embodiment, since the light emitting device 2B and the two light receiving devices 3B and 4B situated at different distances from the light emitting device are provided, individual differences due to differences in skin color among subjects, the scattering coefficient of the fat layer, the condition of contact of the measuring apparatus and the like can be eliminated, so that the subject's body fat percentage or body fat thickness can be excellently measured.

In the present invention it is preferable that the correlation function is made in consideration of weight, age, sex, height and so on of the person.

The portion to be detected can be any portion of the living body. For example arm, belly, shoulder blade are can be portion to be detected.

In the above description one portion of the living body is detected but a plurality of portion of the living body can be detected in order to improve the thickness or percentage.

While examples using one light emitting portion and two light receiving portions have been described in this embodiment, the present invention is not limited thereto; two light emitting portions and one light receiving portion may be provided. In this case, the light emitting portions are situated at different distances from the light receiving portion to calculate the body fat amount.

The light emitting portion of the present invention corresponds to the light emitting device 2B of this embodiment, the first light receiving portion of the present invention corresponds to the light receiving device 3B of this embodiment, the second light receiving portion of the present invention corresponds to the light receiving portion 43 of this embodiment, and the signal processing operation means of the present invention corresponds to the CPU 6B of this embodiment.

As described above, the present invention can be said to be very effective because the body fat percentage and the subcutaneous fat thickness can be easily measured with high accuracy since individual variation can be suppressed.

Next, another implementation of the present invention will be described.

Preferred embodiments of a living body information measuring apparatus of the present invention will hereinafter be described in detail.

Figure 43:
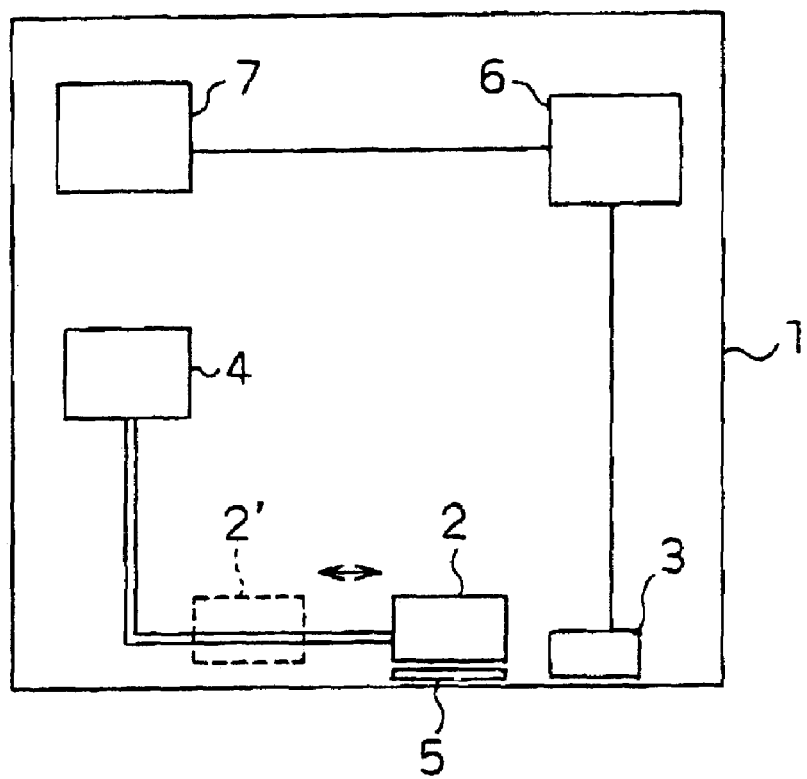
FIG. 43 is a schematic view showing an outline of a body fat measuring apparatus according to an embodiment of the present invention.
Figure 43:
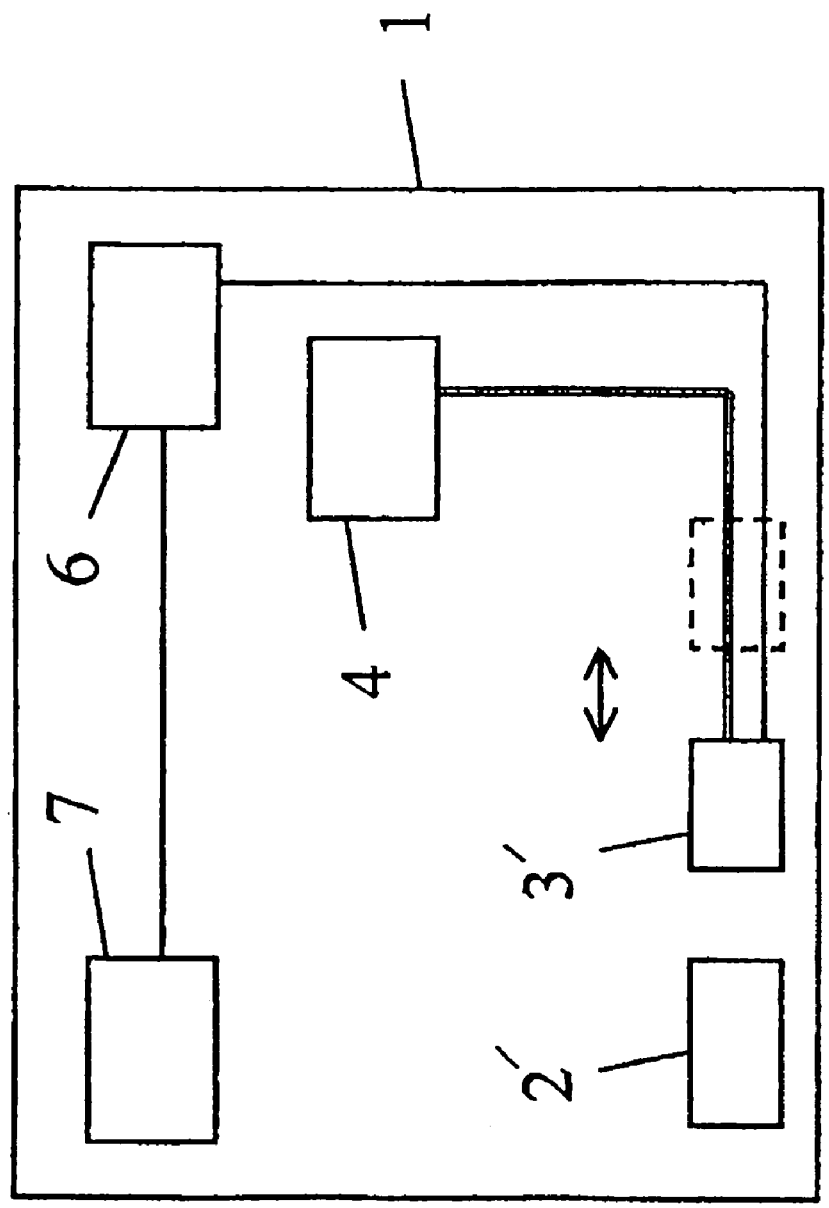

A first embodiment of the present invention will be described with reference to FIG. 43.

A body 1 is provided with a light source 2 for emitting light from an end surface of the body 1, and a light receiving portion 3 having a photoelectric conversion device for detecting the quantity of the light emitted from the light source 2 and having passed through the subject.

As the light source 2, for example, a light emitting diode with a central wavelength of 635 nm (for example, FR1111C manufactured by Stanley) is used.

An attenuating filter 5 for attenuating the light emitted from the light source 2 is disposed below the light source 2.

Reference numeral 4 represents moving means for moving the light source 2 to a position 2', shown by the dotted line in the figure, being farther away from the light receiving portion 3. With this, the distance between the light source 2, 2' and the light receiving portion 3 can be easily changed.

Reference numeral 6 represents a signal processing circuit for processing a signal from the light receiving portion 3 to calculate living body information. Reference numeral 7 represents a display for displaying the values of the living body information.

Next, an example of the measuring method will be described.

The light emitting portion 2 is situated 3 mm away from the light receiving portion 3, and light is projected to the subject from an end surface of the body 1. At this time, it is desirable to attenuate the light quantity by causing the light to pass through the attenuating filter 5.

The light projected to the subject is propagated through the subject's body while being diffuse-reflected, and part of the light reaches the light receiving portion 3. The light quantity value at this time is calculated by the signal processor 6.

Then, the moving means 4 moves the light emitting portion 2 to the position 2' being approximately 9 mm away from the light receiving portion 3. Since the quantity of the light reaching the light receiving portion 3 decreases because of the increase in the distance from the light receiving portion 3, it is desirable not to provide the attenuating filter at the position 2'. That is, the difference between the light quantity in a case where the light emitted from the light emitting portion 2 reaches the light receiving portion 3 and the light quantity in a case where the light emitted from the position 2' of the light receiving portion reaches the light receiving portion 3 is reduced by the provision of the attenuating filter at the position 2, so that saturation does not occur even when the range associated with the light quantity of the photoelectric conversion device serving as the light receiving device of the light receiving portion 3 is small. Needless to say, a known ratio is used as the attenuation ratio of the attenuating filter.

An appropriate attenuation ratio was obtained in the following manner: How light of a wavelength of 650 nm attenuated in the living body was examined for fifteen subjects, and it was found that the light reception quantity at a position 3 mm away from the light emitting portion attenuated to approximately ⅕ at a position 7 mm away, and to approximately to ¹⁄₁₀ at a position 9 mm away.

Therefore, it can be said that when the distance between the light emitting portion and the light receiving portion is changed between 3 mm and 9 mm, it is desirable to attenuate the light quantity to approximately ¹⁄₁₀ by the attenuating filter.

Consequently, the light reception quantities at the two positions are considerably of the same level, so that the range required of the photoelectric conversion device is reduced, which is desirable.

The examination was also performed for cases where wavelengths among 600 nm and 1100 nm were used as the light emission wavelength of the light emitting portion 2, and a substantially similar tendency was shown.

The light emitted from the position 2' of the light emitting portion is diffuse-reflected inside the living body to reach the light receiving portion 3. The quantity of the light having reached the light receiving portion 3 is calculated by the signal processor 6.

The light reception quantity when the light emitting portion is at the position 2' is divided by the light reception quantity when the light emitting portion is at the position 2 by the signal processor 6. Using this value, living body information is calculated, and the result is displayed on the display 7. Details thereof are as described above.

Generally, the light emission characteristic of the light emitting portion 2 varies in the stage of manufacture.

Moreover, the light emission intensity characteristic changes during use due to the temperature, with time and for other reasons.

Moreover, the sensitivity characteristic of the light receiving portion 3 also varies in the stage of manufacture, and it is known that the sensitivity thereof changes with time and the characteristic thereof changes due to the temperature.

However, these problems can be solved by using the above-described embodiment.

Let the light quantity measured by the light receiving portion 3 when the light emitting portion 2 is set above the attenuating means 5 be P3 and the light quantity measured when the light emitting portion is moved to the position 2' by the moving means 4 be P4.

Moreover, it is assumed that the light emission intensity of the light emitting portion 2 changes by L times and the sensitivity of the light receiving portion 3 changes by M times.

At this time, the light quantity measured when the light emitting portion 2 is set above the attenuating means 5 changes from P3 to P3×L×M, and the light quantity measured when the light emitting portion is moved to the position 2' changes from P4 to P4×L×M.

In the present invention, these can be canceled because one signal value is divided by the other to calculate living body information. That is, performing the division, $$(P3 \times L \times M)/(P4 \times L \times M) = P3/P4$$

Consequently, it is apparent that even if the light quantity of the light source or the sensitivity of the light receiving portion changes, living body information not affected by the change can be measured.

According to this embodiment, the above-mentioned problems can be solved by moving the light emitting portion, measuring the light quantity at each position and dividing one light quantity from the other to obtain living body information. However, even in cases other than the case where the division is performed, since the same light emitting portion is moved, the light source is the same, so that the present invention is more tolerant for changes with time at least in that point than apparatuses having two or more light sources.

Moreover, conventionally performed calibration in which the reflected light from the standard plate is measured every measurement to calibrate it can be omitted. Thus, the apparatus of this embodiment is very convenient.

While an example in which the light emitting portion is moved has been described in this embodiment, the present invention is not limited. In the alternative of FIG. 43', the light receiving portion 3' is moved to measure living body information.

Figure 44:
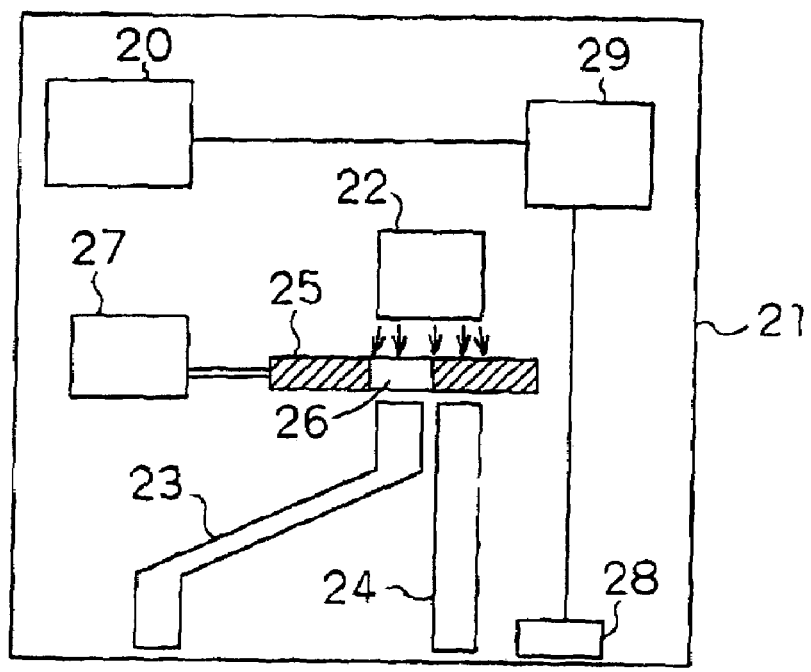
FIG. 44 is a schematic view showing an outline of a living body information measuring apparatus according to another embodiment of the present invention.
Figure 44:
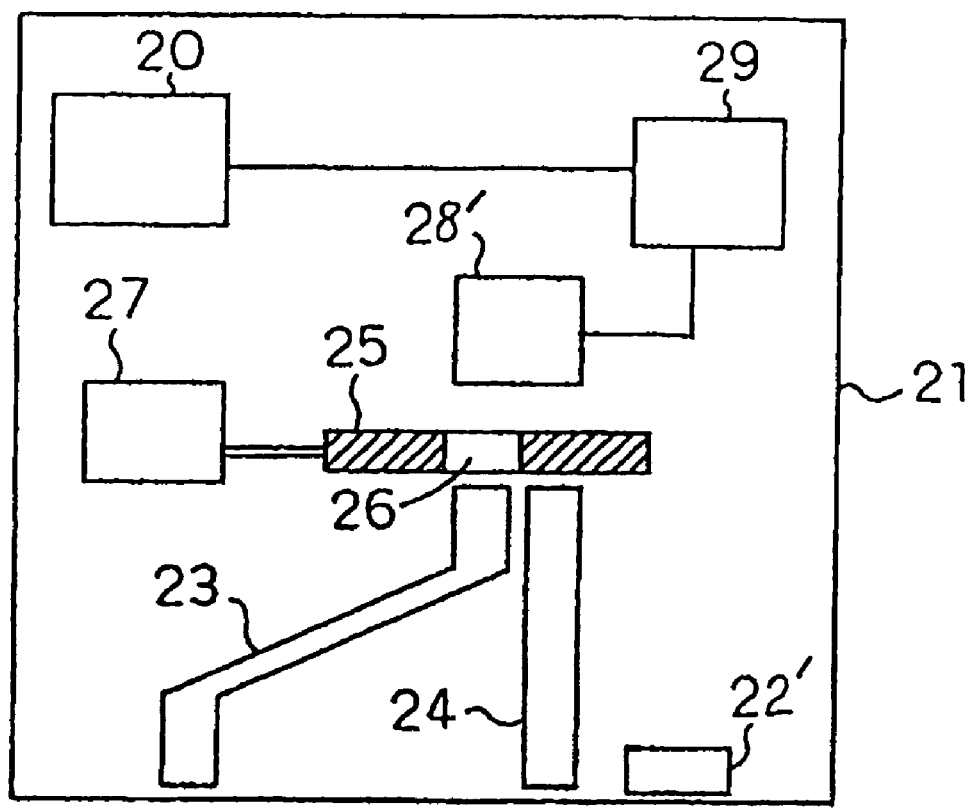
Figure 45:
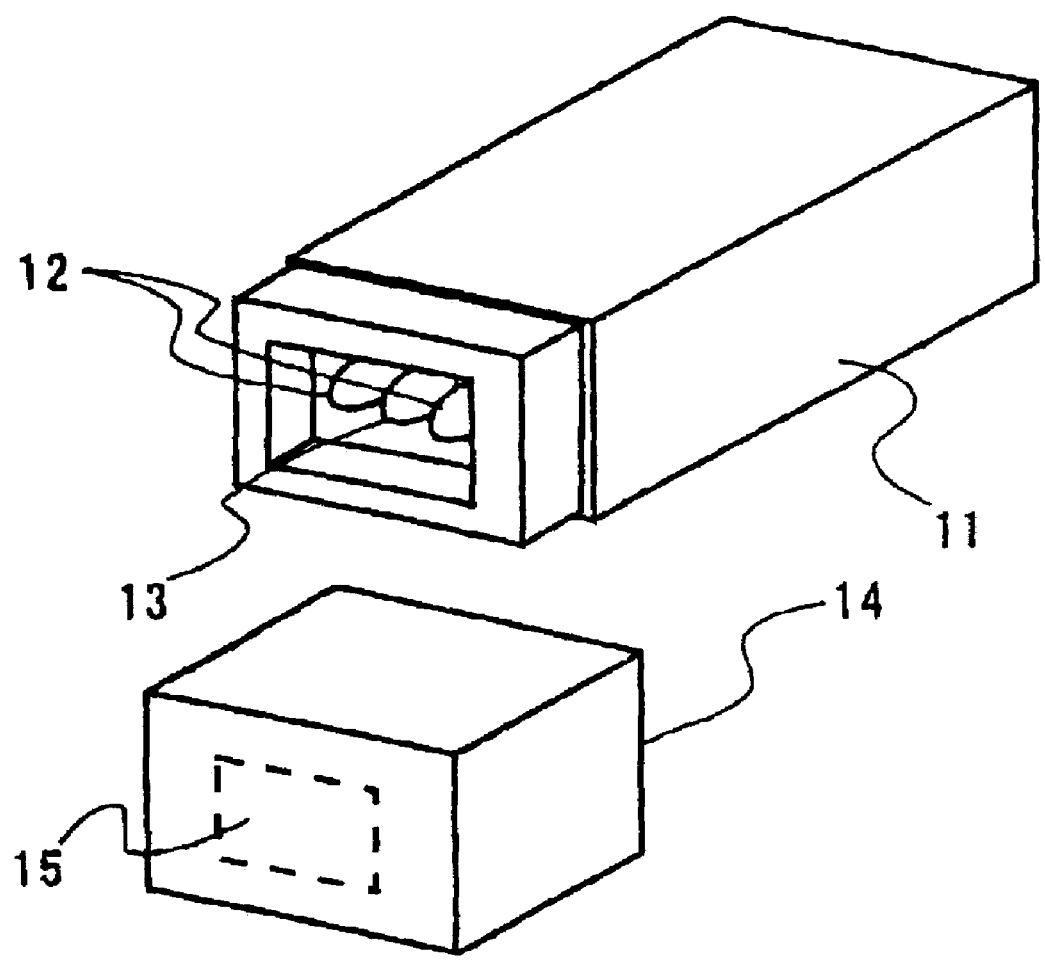
FIG. 45 is a view showing an example of a body fat measuring apparatus according to prior art.

Next, another embodiment of the living body information measuring apparatus of the present invention will be described with reference to FIG. 44.

A body 21 is provided with a light emitting device 22, and light directing means 23 and 24 for directing the light emitted from the light emitting device 22 to an end surface of the body 21. The light directing means 23 and 24 correspond to the optical path of the present invention.

A shutter 25 for selecting light rays to be made incident on the light directing means 23 and 24 from among the light rays emitted from the light source 22 is disposed between the light source 22 and the light directing means 23 and 24. The shutter 25 has a hole 26, and can be moved in a horizontal direction by moving means 27.

For the light directing means 23 and 24, for example, a plastic optical fiber or a transparent material such as transparent acrylic resin is used. For the shutter 25, a metal or plastic is used. It is desirable to black the shutter 25 with black anodized aluminum or the like in order that no light is reflected therefrom. The shutter 25 and the light directing means 23 and 24 constitute the optical path adjusting means of the present invention.

Reference numeral 28 represents a light receiving portion having a photoelectric conversion device for detecting the quantity of the light exiting from end surfaces of the light directing means 23 and 24 and passing through the living body while being diffuse-reflected. Reference numeral 29 represents a signal processor for processing electric signals from the light receiving portion 28 to calculate living body information values such as the body fat and the blood-sugar level.

Reference numeral 20 represents a display for displaying the living body information such as the body fat and the blood-sugar level calculated by the signal processor 29.

Next, the operation will be described.

First, the light emitted from the light emitting device 22 is directed only to the light directing means 23 through the hole 26 of the shutter 25, so that the light is projected to the subject from the part being in intimate contact with the end surface of the body 21. At this time, no light is directed to the light directing means 24.

The light receiving portion 28 is situated, for example, approximately 7 mm away from the light exit end surface of the light directing means 23. By setting the distance between the light receiving portion 28 and the light exit end surface of the light directing means 23 to 7 mm, information on a comparatively deep part of the living body can be measured.

The light having reached the light receiving portion 28 is converted into an electric signal and sent to the signal processing means 29. Let the measurement value at this time be P3.

Then, the shutter 25 is moved by the moving means 27 so that the hole 26 is situated above the light directing means 24. Consequently, the light emitted from the light emitting portion 22 is directed only to the light directing means 24. At this time, no light is directed to the light directing means 23.

The light exit end surface of the light directing means 24 is situated approximately 3 mm away from the light receiving portion 28.

The projected light intrudes into the subject, and then, part of the light is scattered and repetitively reflected to exit from the surface of the living body. Unlike the light exiting from the end surface of the light directing means 23, much of the light having propagated through the vicinity of the surface of the living body can be detected because the distance from the light receiving portion 28 is a comparatively short distance of 3 mm.

The light detected by the light receiving portion 28 is also converted into an electric signal and transmitted to the signal processing means 29. Let the measurement value at this time be P4.

Based on the measurement values P3 and P4, P3 is divided by P4 to obtain P3/P4, and living body information is calculated from this value and displayed on the display 20.

By this measuring method, P3/P4 can be easily measured like the previous embodiment and the influence of the change in the intensity of the light source and the change in the sensitivity of the light receiving portion can be suppressed. Thus, this embodiment can be said to be extremely effective.

While a structure in which the light emitting portion 22 is disposed above the light directing means 23 and 24 has been described in the present invention, the present invention is not limited. For example, in the alternative of FIG. 44' the light emitting portion 22' is disposed in the position of the light receiving portion 28 of FIG. 44 and the light receiving portion 28' is disposed in the position of the light emitting portion 22.

In this embodiment, an example has been described in which by moving the shutter 25 by the moving means 27, the quantity of the light incident on the light directing means 23 and 24 is selected to thereby switch the path of the light.

However, the present invention is not limited thereto; the light emitting portion 22 may be moved to choose between the light directing means 23 and 24.

In this embodiment, it is very desirable to provide attenuating means at the upper end of the light directing means 24. For example, this can be easily realized, for example, by attaching an attenuating film.

The present invention is also a program recording medium such as a CD-ROM or a DVD being readable by a computer and recording therein a program and/or data for causing a computer to perform all or some of the functions of all or some of the elements of the measuring apparatus of all the above-described implementations of the prevent invention. The read program and/or data performs the functions in conjunction with the computer.

Moreover, the present invention is also a program recording medium such as a CD-ROM or a DVD being readable by a computer and recording therein a program and/or data for causing a computer to perform all or some of the operations of all or some of the steps of the measuring methods of all the above-described implementations of the present invention. The read program and/or data performs the functions in conjunction with the computer.

As described above, according to the present invention, a living body information measuring apparatus capable of easily obtaining living body information with high accuracy can be provided.

Moreover, according to the present invention, since individual variation among subjects can be suppressed, the body fat percentage and the subcutaneous fat thickness can be easily measured with high accuracy. Thus, the present invention can be said to be very effective.

Moreover, according to the present invention, even if characteristics of the light source and the light receiving portion change, the influence of the changes can be suppressed, so that living body information such as the body fat percentage and the subcutaneous fat thickness can be measured with high accuracy.

Moreover, according to the present invention, calibration such as measuring the reflected light from the standard plate every measurement can be omitted. Thus, the present invention can be said to be extremely effective.

What is claimed is:

1. A body fat measuring apparatus comprising:
  a light emitting portion for projecting light rays to a subject's tissue;
  a light receiving portion for detecting, of the light rays, at least one of a transmitted light ray having passed through the subject's tissue and a reflected light ray reflected inside the subject's body; and
  signal processing operation means for calculating at least one of the subject's subcutaneous fat thickness and body fat percentage by performing an operation by use of a detection result of the light receiving portion,
  wherein either the number of light emitting portions or the number of light receiving portions is at least two and wherein the at least two light emitting portions or light receiving portions are situated at different distances from corresponding light receiving portions or light emitting portions;
  wherein the light receiving portion includes a first light receiving portion situated at a predetermined distance from the light emitting portion, and a second light receiving portion situated farther away from the light emitting portion than the first light receiving portion, wherein the first light receiving portion detects the transmitted light ray and the reflected light ray having arrived by way of the subject's skin or skin and a layer in the vicinity thereof, wherein the second light receiving portion detects the transmitted light ray and the reflected light ray having arrived by way of the subject's skin and subcutaneous layer, wherein the signal processing operation means corrects a detection result of the second light receiving portion by a detection result of the first light receiving portion and performs an operation by use of a result of the correction to thereby calculate the subject's subcutaneous fat thickness or body fat percentage, wherein the signal processing operation means analyzes all or some light components of wavelengths of substantially 600 to 660 nm, and wherein the distance between the first light receiving portion and the second light receiving portion is at least 2 mm.

2. A body fat measuring apparatus comprising:

a light emitting portion for projecting light rays to a subject's tissue;

a light receiving portion for detecting, of the light rays, at least one of a transmitted light ray having passed through the subject's tissue and a reflected light ray reflected inside the subject's body; and signal processing operation means for calculating at least one of the subject's subcutaneous fat thickness and body fat percentage by performing an operation by use of a detection result of the light receiving portion, wherein either the number of light emitting portions or the number of light receiving portions is at least two and wherein the at least two light emitting portions or light receiving portions are situated at different distances from corresponding light receiving portions or light emitting portions;

wherein the light receiving portion includes a first light receiving portion situated at a predetermined distance from the light emitting portion, and a second light receiving portion situated farther away from the light emitting portion than the first light receiving portion, wherein the first light receiving portion detects the transmitted light ray and the reflected light ray having arrived by way of the subject's skin or skin and a layer in the vicinity thereof, wherein the second light receiving portion detects the transmitted light ray and the reflected light ray having arrived by way of the subject's skin and subcutaneous layer, wherein the signal processing operation means corrects a detection result of the second light receiving portion by a detection result of the first light receiving portion and performs an operation by use of a result of the correction to thereby calculate the subject's subcutaneous fat thickness or body fat percentage, and wherein a central wavelength of the light projected from the light emitting portion is 650 nm.

3. A body fat measuring apparatus comprising:

a light emitting portion for projecting light rays to a subject's tissue;

a light receiving portion for detecting, of the light rays, at least one of a transmitted light ray having passed through the subject's tissue and a reflected light ray reflected inside the subject's body; and signal processing operation means for calculating at least one of the subject's subcutaneous fat thickness and body fat percentage by performing an operation by use of a detection result of the light receiving portion, wherein either the number of light emitting portions or the number of light receiving portions is at least two and wherein the at least two light emitting portions or light receiving portions are situated at different distances from corresponding light receiving portions or light emitting portions;

wherein the light emitting portion includes a first light emitting portion situated at a predetermined distance from the light receiving portion, and a second light emitting portion situated farther away from the light receiving portion than the first light emitting portion, wherein the light receiving portion detects a light ray projected from the first light emitting portion as at least one of a first transmitted light ray and a reflected ray having passed through the subject's skin or skin and a layer in the vicinity thereof, and detects a light ray projected from the second light emitting portion as at least one of a second transmitted light ray and a reflected light ray having passed through the subject's skin and subcutaneous fat layer and a reflected light ray, wherein the signal processing operation means corrects a detection result obtained by the second light emitting portion and the light receiving portion by a detection result obtained by the first light emitting portion and the light receiving portion and performs an operation by use of a result of the correction to thereby calculate the subject's subcutaneous fat thickness or body fat percentage, wherein the signal processing operation means analyzes light components of wavelengths of substantially 600 to 660 nm, and wherein the distance between the first light emitting portion and the second light emitting portion is at least 2 mm.

4. A body fat measuring apparatus comprising:

a light emitting portion for projecting light rays to a subject's tissue;

a light receiving portion for detecting, of the light rays, at least one of a transmitted light ray having passed through the subject's tissue and a reflected light ray reflected inside the subject's body; and signal processing operation means for calculating at least one of the subject's subcutaneous fat thickness and body fat percentage by performing an operation by use of a detection result of the light receiving portion, wherein either the number of light emitting portions or the number of light receiving portions is at least two and wherein the at least two light emitting portions or light receiving portions are situated at different distances from corresponding light receiving portions or light emitting portions;

wherein the light emitting portion includes a first light emitting portion situated at a predetermined distance from the light receiving portion, and a second light emitting portion situated farther away from the light receiving portion than the first light emitting portion, wherein the light receiving portion detects a light ray projected from the first light emitting portion as at least one of a first transmitted light ray and a reflected ray having passed through the subject's skin or skin and a layer in the vicinity thereof, and detects a light ray projected from the second light emitting portion as at least one of a second transmitted light ray and a reflected light ray having passed through the subject's skin and subcutaneous fat layer and a reflected light ray, wherein the signal processing operation means corrects a detection result obtained by the second light emitting portion and the light receiving portion by a detection result obtained by the first light emitting portion and the light receiving portion and performs an operation by use of a result of the correction to thereby calculate the subject's subcutaneous fat thickness or body fat percentage, and wherein a central wavelength of the light projected by the first and the second light emitting portions is substantially 650 nm.

5. A living body information measuring apparatus comprising:

a light emitting portion including a light source for projecting light rays to a subject's tissue;

a light receiving portion including a photoelectric conversion device for detecting, of the light rays, at least one of a transmitted light ray having passed through the subject's tissue and a reflected light ray reflected inside the subject's body;

signal processing operation means for calculating the subject's living body information by performing an operation by use of a detection result of the light receiving portion; and moving means for moving one of the light source or the photoelectric conversion device, wherein either the number of light emitting portions or the number of light receiving portions is at least two and the at least two light emitting portions or light receiving portions are situated at different distances from corresponding light receiving portions or light emitting portions;

wherein the plurality of light emitting portions are realized by moving the light source by the moving means or the plurality of light receiving portions are realized by moving the photoelectric conversion device; and wherein one output obtained by the light receiving portion and the light emitting portion is corrected by an output obtained by another light receiving portion and the light emitting portion or an output obtained by the light receiving portion and another light emitting portion.

6. A living body information measuring apparatus according to claim 5, wherein attenuating means is provided for attenuating a quantity of light output from, of the plurality of light emitting portions, a light emitting portion closer to the light receiving portion.

7. A living body information measuring apparatus according to claim 6, wherein the attenuating means has a function of attenuating the quantity of the light to 50 to 5%.

8. A living body information measuring apparatus according to claim 6, wherein the attenuating means is made of a transparent resin substrate and an absorbing member attached thereonto.

9. A program recording medium being readable by computer and recording therein a program and data for causing a computer to perform functions of elements of a living body information measuring apparatus according to claim 5.

10. A living body information measuring method using a living body information measuring apparatus according to claim 5, said method comprising:

projecting light rays to the subject by the light emitting portion;

a first step of detecting a transmitted light ray and/or a reflected light ray having arrived by way of the subject's skin and/or skin and a layer in the vicinity thereof;

a second step of detecting a transmitted light ray and/or a reflected light ray having arrived by way of the subject's skin and subcutaneous fat layer; and calculating living body information by the signal processing operation means by correcting a detection result of the second step by a detection result of the first step.

11. A living body information measuring apparatus comprising:

a light emitting portion including a light source for projecting light rays to a subject's tissue;

a light receiving portion including a photoelectric conversion device for detecting, of the light rays, at least one of a transmitted light ray having passed through the subject's tissue and a reflected light ray reflected inside the subject's body;

signal processing operation means for calculating the subject's living body information by performing an operation by use of a detection result of the light receiving portion, a plurality of optical paths provided between the light source and the photoelectric conversion device; and optical path adjusting means for switching among the optical paths such that either the number of light emitting portions or the number of light receiving portions is at least two, and the at least two light emitting portions or light receiving portions are situated at different distances from corresponding light receiving portions or light emitting portions, wherein one output obtained by the light receiving portion and the light emitting portion is corrected by an output obtained by another light receiving portion and the light emitting portion or an output obtained by the light receiving portion and another light emitting portion.

12. A living body information measuring apparatus according to claim 11, wherein the optical path adjusting means includes a movable shutter disposed in front of the light source or the photoelectric conversion device and having a hole and a plurality of optical path members derived from the shutter.

13. A living body information measuring apparatus according to claim 11, wherein the optical paths are made of an optical fiber or an acrylic resin.

14. A program recording medium being readable by a computer and recording therein a program and data for causing a computer to perform functions of elements of a living body information measuring apparatus according to claim 11.

15. A living body information measuring method using a living body information measuring apparatus according to claim 11, said living body information measuring method comprising the steps of:
  projecting light rays to the subject by the light emitting portion;
  a first step of detecting a transmitted light ray and/or a reflected light ray having arrived by way of the subject's skin and/or skin and a layer in the vicinity thereof;
  a second step of detecting a transmitted light ray and/or a reflected light ray having arrived by way of the subject's skin and subcutaneous fat layer; and
  calculating living body information by the signal processing operation means by correcting a detection result of the second step by a detection result of the first step.

* * * * *